(12) United States Patent
Shen et al.

(10) Patent No.: US 11,739,090 B2
(45) Date of Patent: Aug. 29, 2023

(54) SUBSTITUTED PYRAZLO[3,4-C]PYRIDINES AS SELECTIVE BTK KINASE INHIBITORS

(71) Applicant: JUMBO DRUG BANK CO., LTD., Sichuan (CN)

(72) Inventors: Chunli Shen, Shanghai (CN); XiaWei Wei, Sichuan (CN); Chengde Wu, Shanghai (CN); Guoping Hu, Shanghai (CN); Ning Jiang, Sichuan (CN); Wei Zheng, Sichuan (CN); Jian Li, Shanghai (CN); Shuhui Chen, Shanghai (CN)

(73) Assignee: JUMBO DRUG BANK CO., LTD., Sichuan (CN)

( * ) Notice: Subject to any disclaimer, the term of this patent is extended or adjusted under 35 U.S.C. 154(b) by 0 days.

(21) Appl. No.: 17/763,732

(22) PCT Filed: Sep. 25, 2020

(86) PCT No.: PCT/CN2020/117690
§ 371 (c)(1),
(2) Date: Mar. 25, 2022

(87) PCT Pub. No.: WO2021/057893
PCT Pub. Date: Apr. 1, 2021

(65) Prior Publication Data
US 2022/0324864 A1 Oct. 13, 2022

(30) Foreign Application Priority Data

Sep. 26, 2019 (CN) .......................... 201910919180.6
Apr. 24, 2020 (CN) .......................... 202010330226.3

(51) Int. Cl.
*A61K 31/437* (2006.01)
*C07D 471/04* (2006.01)
(52) U.S. Cl.
CPC ................................. *C07D 471/04* (2013.01)
(58) Field of Classification Search
CPC ......................... A61K 31/417; C07D 471/04
USPC ......................................... 514/303; 546/119
See application file for complete search history.

(56) References Cited

U.S. PATENT DOCUMENTS

| | | | |
|---|---|---|---|
| 2014/0142213 A1 | 5/2014 | Weiss et al. | |
| 2016/0311820 A1 | 10/2016 | Liu et al. | |
| 2019/0062328 A1 | 2/2019 | Liao et al. | |
| 2019/0106423 A1 | 4/2019 | Hudson et al. | |

FOREIGN PATENT DOCUMENTS

| | | |
|---|---|---|
| CN | 105017256 A | 11/2015 |
| CN | 105399756 A | 3/2016 |
| CN | 110272416 A | 9/2019 |
| JP | 2014520866 A | 8/2014 |
| JP | 2019502763 A | 1/2019 |
| JP | 2019507793 A | 3/2019 |
| WO | 2015095099 A1 | 6/2015 |
| WO | 2016106627 A1 | 7/2016 |
| WO | 2017/156495 A1 | 9/2017 |
| WO | 2018033091 A1 | 2/2018 |
| WO | 2018092047 A1 | 5/2018 |

OTHER PUBLICATIONS

Nov. 27, 2020 International Search Report issued in International Patent Application No. PCT/CN2020/117690.
Nov. 27, 2020 Written Opinion of the International Searching Authority issued in International Patent Application No. PCT/CN2020/117690.
Jun. 3, 2022 Canadian Office Action issued in Canadian Patent Application No. 3,152,587.
Aug. 24, 2022 Japanese Office Action issued in Japanese Patent Application No. 2022519825.
Sep. 19, 2022 Korean Office Action issued in Korean Patent Application No. 20227013965.
Mar. 17, 2022 European search opinion issued in European Patent Application No. 20867917.
Eurasia Office Action dated Dec. 23, 2022 issued in Eurasia Patent Application No. 202290996.
Dec. 16, 2022 Australian Examination report No. 1 issued in Australian patent Application No. 2020355845.
Nov. 7, 2022 Mexican Office Action issued in Mexican Patent Application No. MX/a/2022/003707.
Nov. 7, 2022 European search opinion issued in European Patent Application No. 20867917.

*Primary Examiner* — Douglas M Willis
(74) *Attorney, Agent, or Firm* — Nath, Goldberg & Meyer; Joshua B. Goldberg

(57) ABSTRACT

Disclosed are a class of BTK kinase inhibitor compounds with a high activity and a high selectivity and the use thereof in the preparation of a drug for treating BTK target-related diseases. Specifically, disclosed are a compound shown as formula (I), and an isomer and a pharmaceutically acceptable salt thereof.

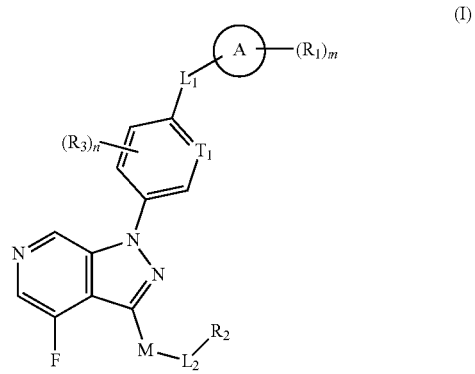

16 Claims, No Drawings

SUBSTITUTED PYRAZLO[3,4-C]PYRIDINES AS SELECTIVE BTK KINASE INHIBITORS

This is a National Phase Application filed under 35 U.S.C. 371 as a national stage of PCT/CN2020/117690, filed Sep. 25, 2020, an application claiming the benefit of Chinese Application No. 201910919180.6, filed Sep. 26, 2019, and Chinese Application No. 202010330226.3, filed Apr. 24, 2020, the content of each of which is hereby incorporated by reference in its entirety. The present application claims the right of priority for
CN 201910919180.6, with filing date: 26 Sep. 2019;
CN 202010330226.3, with filing date: 24 Apr. 2020.
Field of the invention The present disclosure relates to a class of BTK kinase inhibitor compounds with a high activity and a high selectivity and the use thereof in the preparation of a drug for treating BTK target-related diseases. Specifically, the present invention relates to a compound represented by formula (I), an isomer thereof or a pharmaceutically acceptable salt thereof.

BACKGROUND

BTK is a key kinase in the B cell antigen receptor (BCR) signaling pathway. Irreversible BTK inhibitors inhibit BTK activity by covalently binding to the active site Cys-481 of the kinase, thereby effectively inhibiting the excessive proliferation of B cells and achieving anti-tumor or anti-inflammatory effects.

Among the currently marketed drugs, ibrutinib, an irreversible BTK inhibitor jointly developed by Pharmacyclis and Johnson & Johnson, has been approved by FDA for the treatment of mantle cell lymphoma, chronic lymphocytic leukemia, Waldenstrom's macroglobulinemia, chronic graft versus host disease, etc. However, in addition to BTK, irutinib also has strong inhibitory effects on other kinases, especially on kinases such as EGFR, ITK and TEC, which can lead to serious adverse reactions such as rash, diarrhea and bleeding. Therefore, there is a need in the art to develop a new class of BTK inhibitors with a high activity and a good selectivity for the treatment of related diseases.

BRIEF SUMMARY OF THE INVENTION

The present disclosure provides a compound shown as formula (I), an isomer thereof or a pharmaceutically acceptable salt thereof,

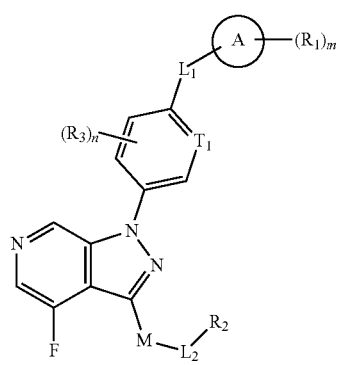

(I)

wherein
$T_1$ is independently selected from N and CH;
$R_2$ is independently selected from H, $C_{1-6}$ alkyl, $C_{2-6}$ alkenyl and $C_{2-6}$ alkynyl, wherein the $C_{1-6}$ alkyl, $C_{2-6}$ alkenyl and $C_{2-6}$ alkynyl are each independently and optionally substituted with 1, 2 or 3 $R_a$;
ring A is selected from phenyl and 5- to 6-membered heteroaryl;
M is independently selected from $C_{3-6}$ cycloalkyl and 3- to 6-membered heterocycloalkyl, wherein the $C_{3-6}$ cycloalkyl and 3- to 6-membered heterocycloalkyl are each independently and optionally substituted with 1, 2 or 3 $R_b$;
$R_1$ and $R_3$ are each independently selected from F, Cl, Br, I, OH, $NH_2$, CN;
n and m are each independently selected from 0, 1, 2 or 3, and n and m are not 0 at the same time;
$L_1$ and $L_2$ are each independently selected from $-CH_2-$, $-CH_2CH_2-$, $-O-$, $-C(=O)-$ and $-C(=O)-NH-$;
$R_a$ is independently selected from H, F, Cl, Br, I, OH, $NH_2$, CN, $C_{1-3}$ alkyl, $C_{1-3}$ alkoxy and $C_{1-3}$ alkylamino, wherein the $C_{1-3}$ alkyl, $C_{1-3}$ alkoxy and $C_{1-3}$ alkylamino are each independently and optionally substituted with 1, 2 or 3 R;
$R_b$ is selected from F, Cl, Br, I, $CH_3$;
R is selected from H, F, Cl, Br, I;
the 5- to 6-membered heteroaryl and 3- to 6-membered heterocycloalkyl each independently comprise 1, 2, 3 or 4 heteroatoms or heteroatomic groups independently selected from $-NH-$, $-O-$, $-S-$, $-C(=O)-$, $-S(=O)-$ and N.

The present disclosure provides a compound shown as formula (I), an isomer thereof or a pharmaceutically acceptable salt thereof,

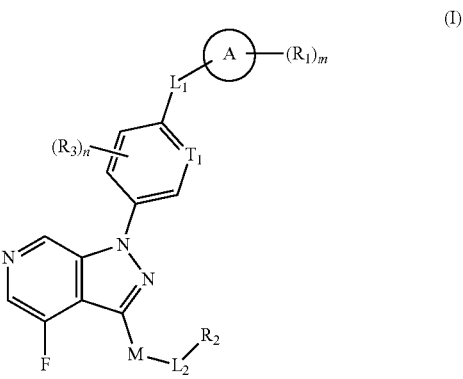

(I)

wherein
$T_1$ is independently selected from N and CH;
$R_2$ is independently selected from H, $C_{1-6}$ alkyl, $C_{2-6}$ alkenyl and $C_{2-6}$ alkynyl, wherein the $C_{1-6}$ alkyl, $C_{2-6}$ alkenyl and $C_{2-6}$ alkynyl are each independently and optionally substituted with 1, 2 or 3 $R_a$;
ring A is selected from phenyl and 5- to 6-membered heteroaryl;
M is independently selected from $C_{3-6}$ cycloalkyl and 3- to 6-membered heterocycloalkyl, wherein the $C_{3-6}$ cycloalkyl and 3- to 6-membered heterocycloalkyl are each independently and optionally substituted with 1, 2 or 3 $R_b$;
$R_1$ and $R_3$ are each independently selected from F, Cl, Br, I, OH, $NH_2$, CN;

n and m are 0, 1, 2 or 3, and n and m are not 0 at the same time;

L$_1$ and L$_2$ are each independently selected from —CH$_2$—, —CH$_2$CH$_2$—, —O—, —C(O)— and —C(O)NH—;

R$_a$ is selected from H, F, Cl, Br, I, OH, NH$_2$, CN, C$_{1-3}$ alkyl, C$_{1-3}$ alkoxy and C$_{1-3}$ alkylamino, wherein the C$_{1-3}$ alkyl, C$_{1-3}$ alkoxy and C$_{1-3}$ alkylamino are each independently and optionally substituted with 1, 2 or 3 R;

R$_b$ is selected from F, Cl, Br, I, CH$_3$;

R is selected from H, F, Cl, Br, I.

the 5- to 6-membered heteroaryl and 3- to 6-membered heterocycloalkyl each independently comprise 1, 2, 3 or 4 heteroatoms or heteroatomic groups independently selected from —NH—, —O—, —S—, —C(═O)—, —S(═O)— and N.

In some embodiments of the present disclosure, the above-mentioned R$_a$ is independently selected from H, F, Cl, Br, I, OH, NH$_2$, CN, CH$_3$, OCH$_3$, NH(CH$_3$) and N(CH$_3$)$_2$, and other variables are as defined in the present disclosure.

In some embodiments of the present disclosure, the above-mentioned R$_2$ is independently selected from H, C$_{1-3}$ alkyl, C$_{2-4}$ alkenyl and C$_{2-4}$ alkynyl, wherein the C$_{1-3}$ alkyl, C$_{2-4}$ alkenyl and C$_{2-4}$ alkynyl are each independently and optionally substituted with 1, 2 or 3 R$_a$, and other variables are as defined in the present disclosure.

In some embodiments of the present disclosure, the above-mentioned R$_2$ is independently selected from H, CH$_3$, vinyl and propynyl, and other variables are as defined in the present disclosure.

In some embodiments of the present disclosure, the above-mentioned M is independently selected from cyclopropyl, cyclobutyl, cyclopentyl, cyclohexyl, azetidinyl, oxetanyl, piperidyl and morpholinyl, wherein the cyclopropyl, cyclobutyl, cyclopentyl, cyclohexyl, azetidinyl, oxetanyl, piperidyl, morpholinyl are each independently and optionally substituted with 1, 2 or 3 R$_b$, and other variables are as defined in the present disclosure.

In some embodiments of the present disclosure, the above-mentioned M is selected from cyclopropyl, cyclobutyl, cyclopentyl, cyclohexyl, azetidinyl, oxetanyl, piperidyl and morpholinyl, wherein the cyclopropyl, cyclobutyl, cyclopentyl, cyclohexyl, azetidinyl, oxetanyl, piperidyl, morpholinyl are each independently and optionally substituted with 1, 2 or 3 R$_b$, and other variables are as defined in the present disclosure.

In some embodiments of the present disclosure, the above-mentioned M is independently selected from piperidyl and morpholinyl, and other variables are as defined in the present disclosure.

In some embodiments of the present disclosure, the above-mentioned M is selected from piperidyl and morpholinyl, and other variables are as defined in the present disclosure.

In some embodiments of the present disclosure, the above-mentioned L$_1$ is selected from —O— and —C(O)NH—, and other variables are as defined in the present disclosure.

In some embodiments of the present disclosure, the above-mentioned L$_1$ is selected from —O— and —C(═O)—NH—, and other variables are as defined in the present disclosure.

In some embodiments of the present disclosure, the above-mentioned L$_2$ is selected from —C(═O)— and —C(═O)—NH—, and other variables are as defined in the present disclosure.

In some embodiments of the present disclosure, the above-mentioned L$_2$ is selected from —C(O)— and —C(O)NH—, and other variables are as defined in the present disclosure.

In some embodiments of the present disclosure, the above-mentioned ring A is selected from phenyl and pyridyl, and other variables are as defined in the present disclosure.

In some embodiments of the present disclosure, the above-mentioned structural unit is

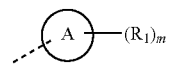

selected from

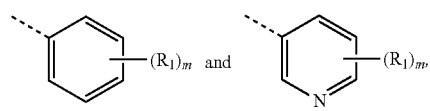

and other variables are as defined in the present disclosure.

In some embodiments of the present disclosure, the above-mentioned structural unit

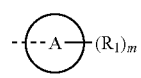

is selected from

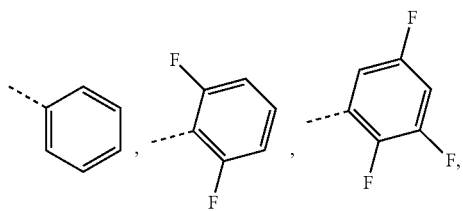

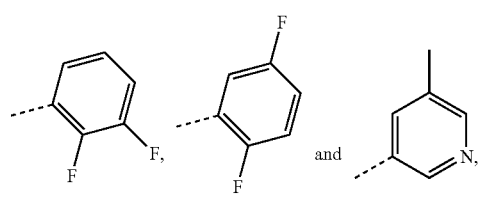

and other variables are as defined in the present disclosure.

Other embodiments of the present disclosure are generated by any combination of the above-mentioned variables.

In some embodiments of the present disclosure, the above-mentioned compound, isomer thereof or pharmaceutically acceptable salt thereof is selected from

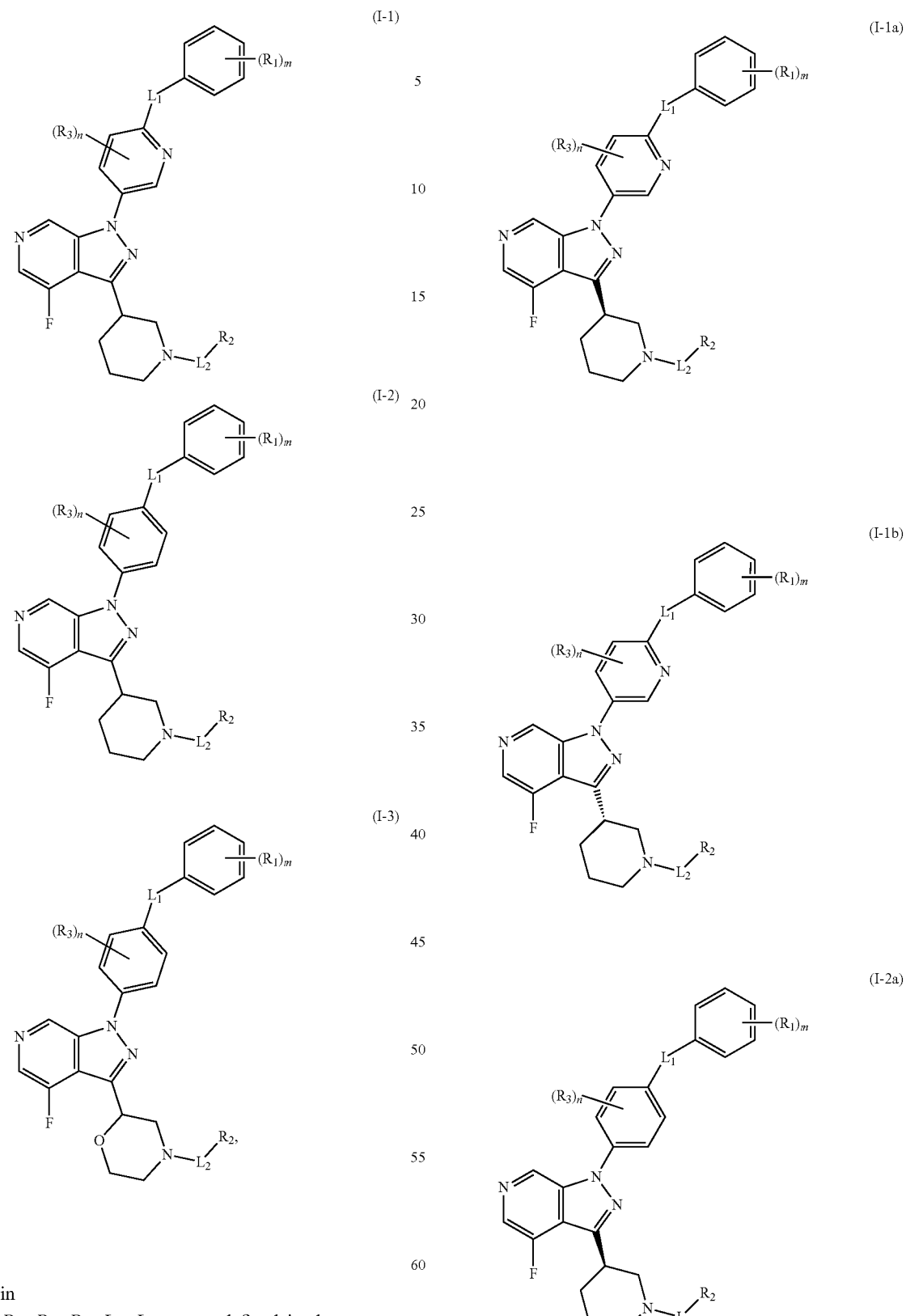
wherein
n, m, $R_1$, $R_2$, $R_3$, $L_1$, $L_2$ are as defined in the present disclosure.
In some embodiments of the present disclosure, the above-mentioned compound, isomer thereof or pharmaceutically acceptable salt thereof is selected from

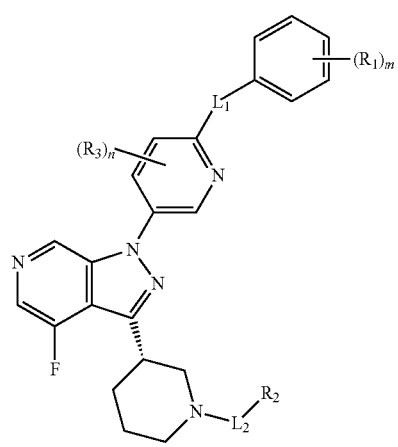
(I-2b)
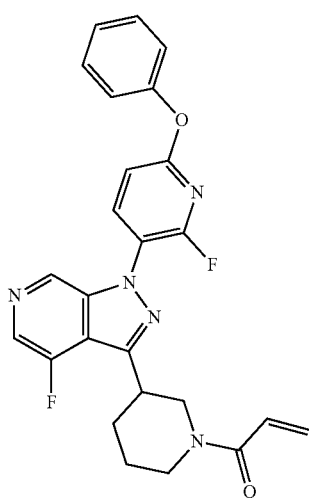
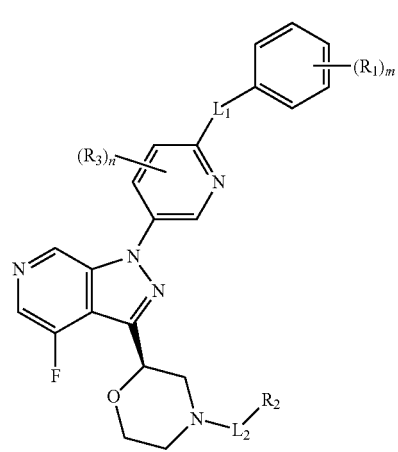
(I-3a)
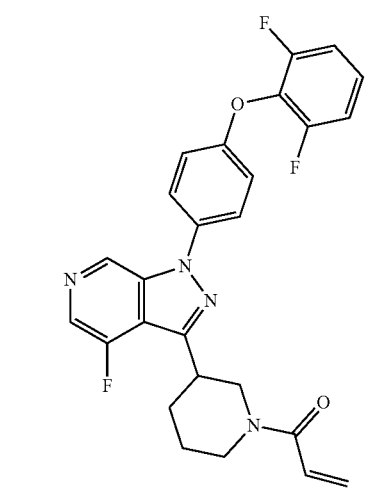
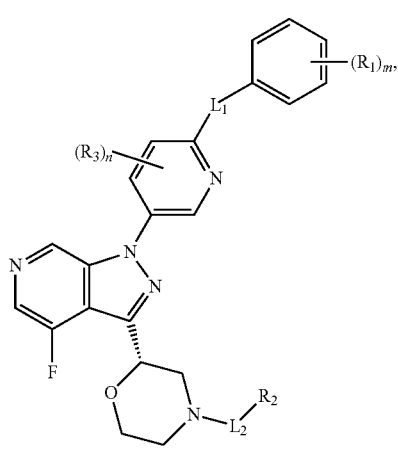
(I-3b)
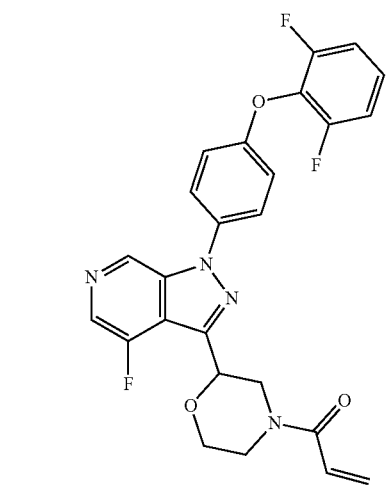
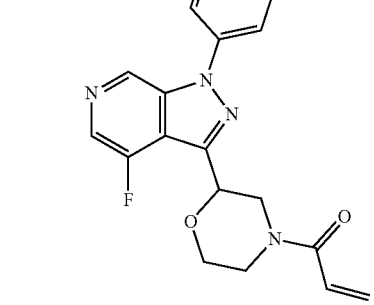
wherein
n, m, $R_1$, $R_2$, $R_3$, $L_1$, $L_2$ are as defined in the present disclosure.
The present disclosure also provides a compound as shown in the following formulas, an isomer thereof or a pharmaceutically acceptable salt thereof,

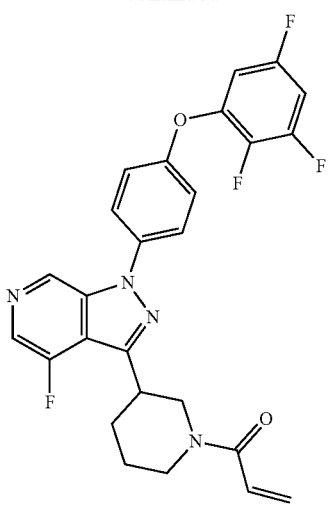
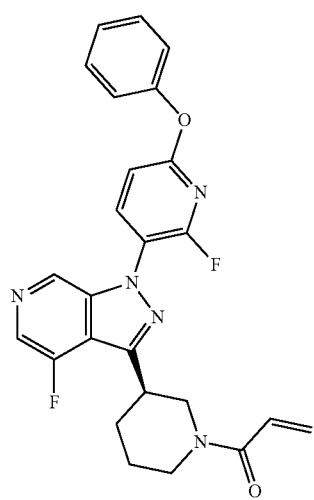
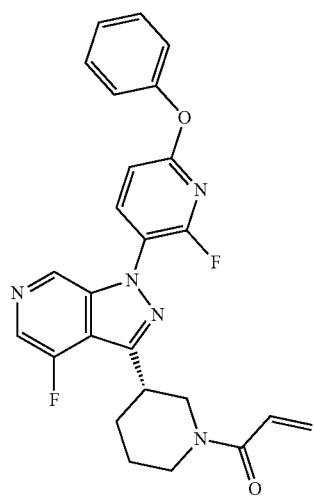
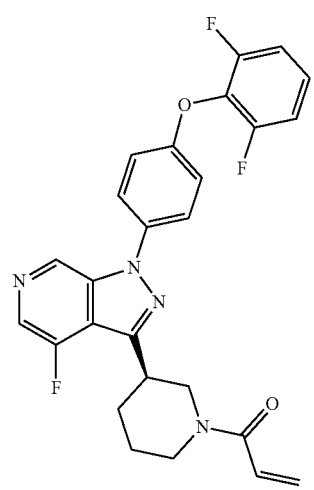
In some embodiments of the present disclosure, the above-mentioned compound, isomer thereof or pharmaceutically acceptable salt thereof is selected from

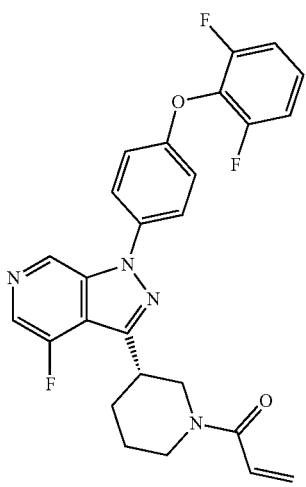
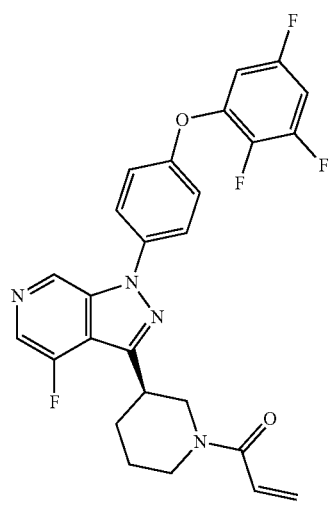
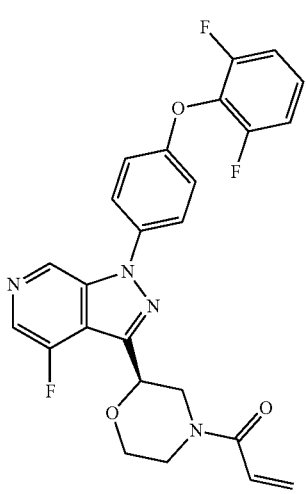
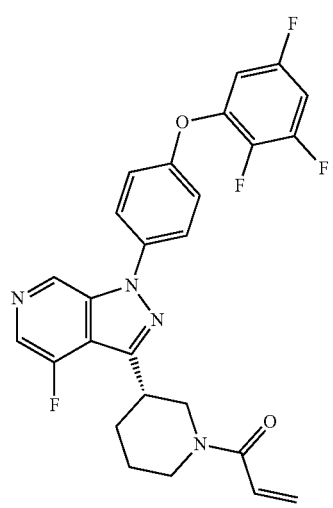
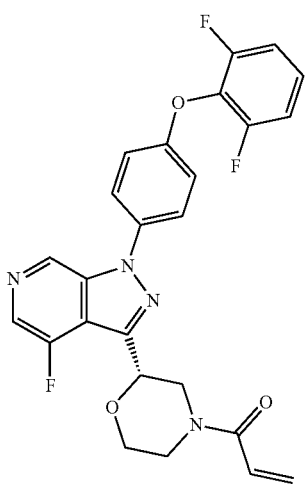

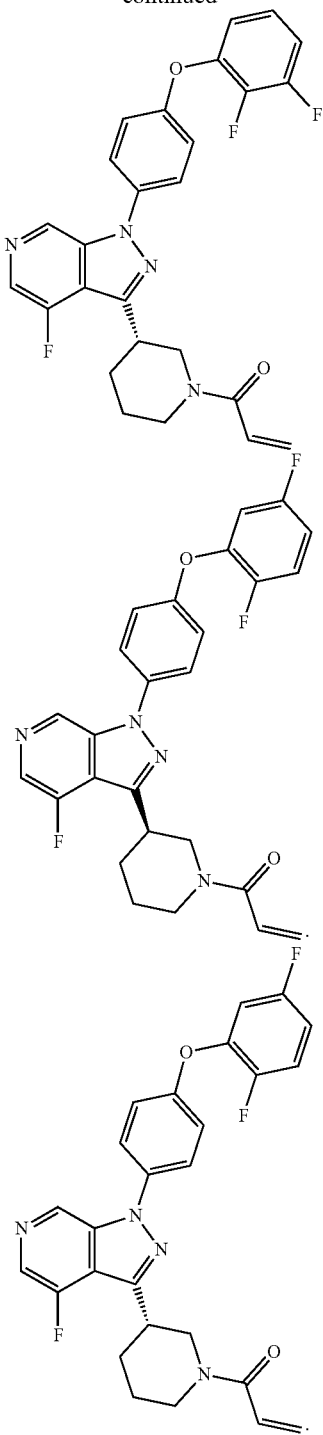

The present disclosure also provides a pharmaceutical composition comprising a therapeutically effective amount of the above-mentioned compound, isomer thereof or pharmaceutically acceptable salt thereof as an active ingredient, and a pharmaceutically acceptable carrier.

In some embodiments of the present disclosure, the above-mentioned compound, isomer thereof or pharmaceutically acceptable salt thereof or the use of the above-mentioned pharmaceutical composition in the preparation of a BTK inhibitor-related drug.

In some embodiments of the present disclosure, the above-mentioned use is characterized in that the BTK inhibitor-related drug is a drug for treating hematological tumor and an autoimmune disease.

In some embodiments of the present disclosure, the above-mentioned use is characterized in that the BTK inhibitor-related is a drug for treating diffuse large B-cell lymphoma.

Technical Effects

The compounds of the present disclosure, as a class of BTK kinase inhibitors with a high activity and a high selectivity, have a great application prospect in the treatment of tumors and show a good effect of inhibiting tumors in the treatment of cancer. The compounds of the present disclosure exhibit a better kinase inhibitory activity, and preferably, the compounds have a strong kinase inhibitory activity ($IC_{50}$<100 nM). The compounds of the present disclosure exhibit a better EGFR, ITK and TEC kinase selectivity. The compounds of the present disclosure have a short half-life, wide distribution outside blood plasma and moderate bioavailability.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof.

The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present disclosure, which is prepared from the compound having specific substituents found in the present disclosure with relatively non-toxic acids or bases. When compounds of the present disclosure contain relatively acidic functional groups, base addition salts can be obtained by contacting such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present disclosure contain relatively basic functional groups, acid addition salts can be obtained by contacting such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and also include salts of amino acids (such as arginine), and salts of organic acids such as glucuronic acid. Certain specific compounds of the present disclosure contain basic and acidic functional groups and thus can be converted to any base or acid addition salt.

The pharmaceutically acceptable salts of the present disclosure can be synthesized from a parent compound containing acid radicals or base radicals by conventional chemical methods. In general, the method for preparing such salts comprises: in water or an organic solvent or a mixture of both, reacting these compounds in free acid or base forms with a stoichiometric amount of a suitable base or acid to prepare the salts.

With respect to a drug or a pharmacological active agent, the term "effective amount" or "therapeutically effective amount" refers to a non-toxic but sufficient amount of the drug or agent to achieve the desired effect. With respect to oral dosage forms of the present disclosure, an "effective amount" of one active substance in a composition refers to an amount required to achieve the desired effect when used in combination with another active substance in the composition. The determination of the effective amount varies with each individual, depending on the age and general conditions of receptors, and also depending on specific active substances, and the appropriate effective amount in an individual case can be determined by a person skilled in the art on the basis of conventional experiments.

The term "active ingredient", "therapeutic agent", "active substance" or "active agent" refers to a chemical entity that can effectively treat target disorders, diseases, or conditions.

The structure of the compound of the present disclosure can be confirmed by conventional methods well known to a person skilled in the art. If the present disclosure relates to the absolute configuration of the compound, the absolute configuration can be confirmed by conventional technical means in the art. For example, single-crystal X-ray diffraction (SXRD) uses a Bruker D8 venture diffractometer to collect the diffraction intensity data of the cultivated single crystal, with a light source of CuKα radiation, and a scanning mode of φ/ω scanning. After the related data is collected, a direct method (Shelxs97) is further used to resolve the crystal structure, so that the absolute configuration can be confirmed.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present disclosure. Additional asymmetric carbon atoms may be present in a substituent such as an alkyl group. All these isomers and mixtures thereof are included in the scope of the present disclosure.

Unless otherwise stated, the term "enantiomer" or "optical isomer" refers to stereoisomers that are mirror images of each other.

Unless otherwise stated, the term "cis-trans isomer" or "geometric isomer" is caused by the fact that double bonds or single bonds of ring-forming carbon atoms cannot rotate freely.

Unless otherwise stated, the term "diastereomer" refers to stereoisomers in which molecules have two or more chiral centers and are not mirror images of each other.

Unless otherwise stated, "(+)" represents right-handed, "(−)" represents left-handed, and "(±)" means racemic.

Unless otherwise stated, the wedge-shaped solid bond ( ) and the wedge-shaped dotted bond ( ) represent the absolute configuration of a stereoscopic center; the straight solid bond ( ) and the straight dotted bond ( ) represent the relative configuration of a stereoscopic center; the wavy line ( ) represents the wedge-shaped solid bond ( ) or the wedge-shaped dotted bond ( ); or the wavy line ( ) represents the straight solid bond ( ) or the straight dotted bond ( ).

Unless otherwise stated, the term "rich in one isomer", "isomer enriched", "rich in one enantiomer" or "enantiomerically enriched" refers to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomers and D and L isomers can be prepared using chiral synthesis or chiral reagents or other conventional techniques. If a particular enantiomer of a compound of the present disclosure is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines).

The compounds of the present disclosure may contain unnatural proportions of atomic isotopes at one or more of the atoms constituting the compound. For example, the compounds may be radiolabeled with radioactive isotopes, such as tritium ($^3H$), iodine-125 ($^{125}I$) or C-14 ($^{14}C$). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present disclosure, whether radioactive or not, are intended to be encompassed within the scope of the present disclosure.

The term "optional" or "optionally" means that the subsequently described event or circumstance may, but not necessarily occur, and that the description includes instances where said event or circumstance occurs and instances where said event or circumstance does not occur.

The term "substituted" means that any one or more hydrogen atoms on the designated atom are substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups. The term "optionally substituted" means that it may or may not be substituted. Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2 R, the group can optionally be substituted with up to two R, and R in each case has independent options. In addition, combinations of substituents and/or variants thereof are permissible only if such combinations result in stable compounds.

When the number of a linking group is 0, such as —(CRR)$_0$—, it means that the linking group is a single bond.

When the number of a substituent is 0, it means that the substituent does not exist. For example, -A-(R)$_0$ means that the structure is actually -A.

When a substituent is vacant, it means that the substituent does not exist. For example, when X is vacant in A-X, it means that the structure is actually A.

When one of the variables is selected from a single bond, it means that the two groups to which it is connected are directly connected. For example, when L represents a single bond in A-L-Z, it means that the structure is actually A-Z.

When the bond of a substituent can be cross-connected to more than two atoms on a ring, the substituent can be bonded to any atom on the ring, for example, the structural unit

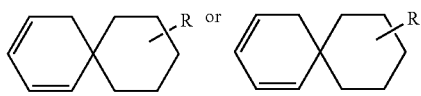

indicates that the substituent R can be substituted at any position on the cyclohexyl or cyclohexadiene. When the substituents listed do not indicate through which atom they are connected to the substituted group, such substituents can be bonded through any of the atoms thereof, for example, pyridyl as a substituent can be attached to the substituted group via any carbon atom on the pyridine ring.

When the linking group listed does not indicate the linking direction thereof, the linking direction is arbitrary, for example, the linking group L is -M-W— in

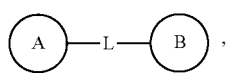

at this situation, -M-W— can connect ring A and ring B in the same direction as the reading order from left to right to form

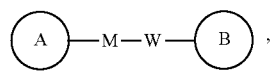

and can also connect ring A and ring B in the opposite direction as the reading order from left to right to form

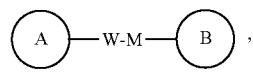

Combinations of the linking groups, substituents, and/or variants thereof are permissible only if such combinations result in stable compounds.

Unless otherwise specified, when a group has one or more connectable sites, any one or more sites of the group can be connected to other groups through chemical bonds. When the connection mode of the chemical bond is not positioned, and there is an H atom at the connectable site, the number of H atoms at the site will decrease correspondingly with the number of chemical bonds connected to become a group with the corresponding valence when the chemical bond is connected. The chemical bonds between the sites and other groups can be represented by a straight solid bond (╱), a straight dotted bond (╱) or a wavy line (～). For example, the straight solid bond in —OCH$_3$ means that the group is connected to other groups through the oxygen atom in the group; the straight dotted bond in

means that the group is connected to other groups through the two ends of the nitrogen atom in the group; the wavy line in

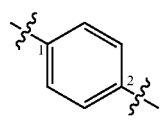

means that the group is connected to other groups through the 1 and 2 carbon atoms in the phenyl group;

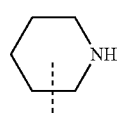

means that any connectable site on the piperidinyl can be connected to other groups through one chemical bond, including at least four connection modes:

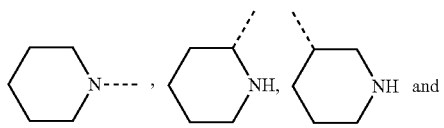

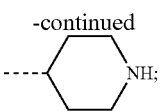

even if the H atom is drawn on —N—,

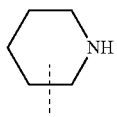

still includes the group of the connection mode

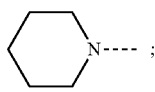

but the H at the site will decrease correspondingly by one and become the corresponding monovalent piperidinyl when one chemical bond is connected.

Unless otherwise specified, the number of atoms in a ring is usually defined as the member number of the ring. For example, "5- to 7-membered ring" means a "ring" with 5-7 atoms arranging in a circle.

Unless otherwise specified, the term "$C_{1-6}$ alkyl" is used to represent a linear or branched saturated hydrocarbon group consisting of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$ and $C_5$ alkyl; and it can be monovalent (such as methyl), divalent (such as methylene) or multivalent (such as methine). Examples of $C_{1-6}$ alkyl include, but are not limited to, methyl (Me), ethyl (Et), propyl (including n-propyl and isopropyl), butyl (including n-butyl, isobutyl, s-butyl and t-butyl), pentyl (including n-pentyl, isopentyl and neopentyl) and hexyl.

Unless otherwise specified, the term "$C_{1-3}$ alkyl" is used to represent a linear or branched saturated hydrocarbon group consisting of 1 to 3 carbon atoms. The $C_{1-3}$ alkyl includes $C_{1-2}$ alkyl, $C_{2-3}$ alkyl, etc.; and it can be monovalent (such as methyl), divalent (such as methylene) or multivalent (such as methine). Examples of $C_{1-3}$ alkyl include, but are not limited to, methyl (Me), ethyl (Et), propyl (including n-propyl and isopropyl), etc.

Unless otherwise specified, the term "halo" or "halogen" by itself or as part of another substituent means a fluorine, chlorine, bromine or iodine atom.

Unless otherwise specified, "$C_{3-6}$ cycloalkyl" means a saturated cyclic hydrocarbon group consisting of 3 to 6 carbon atoms, which comprises a monocyclic and bicyclic ring system, wherein the carbon atoms may be optionally oxidized (i.e., C=O). The $C_{3-6}$ cycloalkyl includes $C_{3-5}$ cycloalkyl, $C_{4-5}$ cycloalkyl, $C_{5-6}$ cycloalkyl, etc.; and it can be monovalent, bivalent or multivalent. Examples of $C_{3-6}$ cycloalkyl include, but are not limited to, cyclopropyl, cyclobutyl, cyclopentyl, cyclohexyl, etc.

Unless otherwise specified, "$C_{2-6}$ alkenyl" is used to represent a linear or branched hydrocarbon group consisting of 2 to 6 carbon atoms comprising at least one carbon-carbon double bond, wherein the carbon-carbon double bond may be located at any position of the group. The $C_{2-6}$ alkenyl includes $C_{2-4}$ alkenyl, $C_{2-3}$ alkenyl, $C_4$ alkenyl, $C_3$ alkenyl, $C_2$ alkenyl, etc.; and it can be monovalent, bivalent or multivalent. Examples of $C_{2-6}$ alkenyl include, but are not limited to vinyl, propenyl, butenyl, pentenyl, hexenyl, butadienyl, piperylene, hexadienyl, etc.

Unless otherwise specified, "$C_{2-4}$ alkenyl" is used to represent a linear or branched hydrocarbon group consisting of 2 to 4 carbon atoms comprising at least one carbon-carbon double bond, wherein the carbon-carbon double bond may be located at any position of the group. The $C_{2-4}$ alkenyl includes $C_{2-3}$ alkenyl, $C_4$ alkenyl, $C_3$ alkenyl, $C_2$ alkenyl, etc.; and the $C_{2-4}$ alkenyl can be monovalent, bivalent or multivalent. Examples of $C_{2-4}$ alkenyl include, but are not limited to vinyl, propenyl, butenyl, butadienyl, etc.

Unless otherwise specified, "$C_{2-6}$ alkynyl" is used to represent a linear or branched hydrocarbon group consisting of 2 to 6 carbon atoms comprising at least one carbon-carbon triple bond, wherein the carbon-carbon triple bond may be located at any position of the group. The $C_{2-6}$ alkynyl includes $C_{2-4}$ alkynyl, $C_{2-3}$ alkynyl, $C_4$ alkynyl, $C_3$ alkynyl, $C_2$ alkynyl, etc.; and it can be monovalent, bivalent or multivalent. Examples of $C_{2-6}$ alkynyl include, but are not limited to ethynyl, propynyl, butynyl, pentynyl, etc.

Unless otherwise specified, "$C_{2-4}$ alkynyl" is used to represent a linear or branched hydrocarbon group consisting of 2 to 4 carbon atoms comprising at least one carbon-carbon triple bond, wherein the carbon-carbon triple bond may be located at any position of the group. The $C_{2-4}$ alkynyl includes $C_{2-3}$ alkynyl, $C_4$ alkynyl, $C_3$ alkynyl, $C_2$ alkynyl, etc.; and it can be monovalent, bivalent or multivalent. Examples of $C_{2-4}$ alkynyl include, but are not limited to ethynyl, propynyl, butynyl, etc.

Unless otherwise specified, the term "$C_{1-3}$ alkoxy" means those alkyl groups comprising 1 to 3 carbon atoms that are connected to the rest of the molecule through one oxygen atom. The $C_{1-3}$ alkoxy includes $C_{1-2}$ alkoxy, $C_{2-3}$ alkoxy, $C_3$ alkoxy, $C_2$ alkoxy, etc. Examples of $C_{1-3}$ alkoxy include, but are not limited to methoxy, ethoxy, propoxy (including n-propoxy and isopropoxy), etc.

Unless otherwise specified, the term "$C_{1-3}$ alkylamino" means those alkyl groups comprising 1 to 3 carbon atoms that are connected to the rest of the molecule through an amino group. The $C_{1-3}$ alkylamino includes $C_{1-2}$, $C_3$, $C_2$ alkylamino, etc. Examples of $C_{1-3}$ alkylamino include, but are not limited to —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$, etc.

Unless otherwise specified, the term "3- to 6-membered heterocycloalkyl" by itself or in combination with other terms respectively represents a saturated cyclic group consisting of 3 to 6 ring atoms, of which 1, 2, 3 or 4 ring atoms are heteroatoms independently selected from O, S and N, and the rest of which are carbon atoms, wherein the nitrogen atom is optionally quaternized, and the nitrogen and sulfur heteroatoms can be optionally oxidized (i.e., NO and S(O)$_p$, wherein p is 1 or 2). It comprises a monocyclic and bicyclic ring system, wherein the bicyclic system includes a spiro ring, a fused ring, and a bridged ring. In addition, in terms of the "3- to 6-membered heterocycloalkyl", the heteroatom may occupy the position at which the heterocycloalkyl is connected to the rest of the molecule. The 3- to 6-membered heterocycloalkyl includes 4- to 6-membered, 5- to 6-membered, 4-membered, 5-membered, 6-membered heterocycloalkyl, etc. Examples of 3- to 6-membered heterocycloalkyl include, but are not limited to, azetidinyl, oxetanyl, thiatanyl, pyrrolidinyl, pyrazolidinyl, imidazolidinyl, tetrahydrothienyl (including tetrahydrothien-2-yl, tetrahydrothien-3-yl, etc.), tetrahydrofuranyl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl or homopiperidinyl.

Unless otherwise specified, the terms "5- to 6-membered heteroaryl ring" and "5- to 6-membered heteroaryl" of the present disclosure can be used interchangeably, and the term "5- to 6-membered heteroaryl" represents a monocyclic group having a conjugated π-electron system and consisting of 5 to 6 ring atoms, of which 1, 2, 3 or 4 ring atoms are heteroatoms independently selected from O, S and N, and the rest of which are carbon atoms, wherein the nitrogen atom is optionally quaternized, and the carbon, nitrogen and sulfur heteroatoms may be optionally oxidized (i.e., C=O, NO and $S(O)_p$, wherein p is 1 or 2). The 5- to 6-membered heteroaryl can be connected to the rest of the molecule through a heteroatom or a carbon atom. The 5- to 6-membered heteroaryl includes 5-membered and 6-membered heteroaryl. Examples of the 5- to 6-membered heteroaryl include, but are not limited to, pyrrolyl (including N-pyrrolyl, 2-pyrrolyl, 3-pyrrolyl, etc.), pyrazolyl (including 2-pyrazolyl, 3-pyrazolyl, etc.), imidazolyl (including N-imidazolyl, 2-imidazolyl, 4-imidazolyl, 5-imidazolyl, etc.), oxazolyl (including 2-oxazolyl, 4-oxazolyl, 5-oxazolyl, etc.), triazolyl (1H-1,2,3-triazolyl, 2H-1,2,3-triazolyl, 1H-1,2,4-triazolyl, 4H-1,2,4-triazolyl, etc.), tetrazolyl, isoxazolyl (including 3-isoxazolyl, 4-isoxazolyl, 5-isoxazolyl, etc.), thiazolyl (including 2-thiazolyl, 4-thiazolyl, 5-thiazolyl, etc.), furyl (including 2-furanyl, 3-furanyl, etc.), thienyl (including 2-thienyl, 3-thienyl, etc.), pyridyl (including 2-pyridyl, 3-pyridyl, 4-pyridyl, etc.), pyrazinyl or pyrimidinyl (including 2-pyrimidyl, 4-pyrimidyl, etc.).

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The solvents used in the present disclosure are commercially available.

The present disclosure uses the following abbreviations: aq represents water; eq represents equivalent; DCM represents dichloromethane; PE represents petroleum ether; DMF represents N,N-dimethylformamide; DMSO represents dimethyl sulfoxide; EtOAc represents ethyl acetate; EtOH represents ethanol; MeOH represents methanol; Cbz represents benzyloxycarbonyl, which is an amine protecting group; Boc represents tertbutoxycarbonyl, which is an amine protecting group; HOAc represents acetic acid; THF represents tetrahydrofuran; LDA represents lithium diisopropylamide.

Compounds are named according to conventional naming principles in the field or using ChemDraw® software, and commercially available compounds are named using supplier catalog names.

DETAILED DESCRIPTION

The present disclosure will be described in detail with the following examples, but not imply any adverse limitation to the present disclosure. The present disclosure has been described in detail herein, and the specific embodiments thereof are also disclosed therein. For a person skilled in the art, without departing from the spirit and scope of the present disclosure, all the variations and improvements made to the specific embodiments of the present disclosure would have been obvious.

Example 1

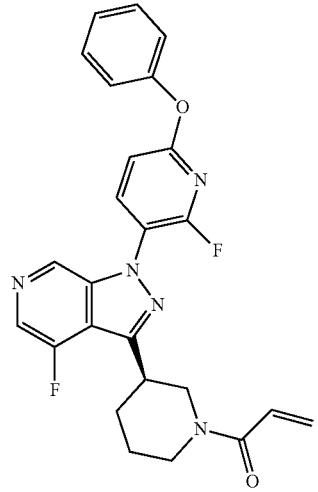

1A or 1B

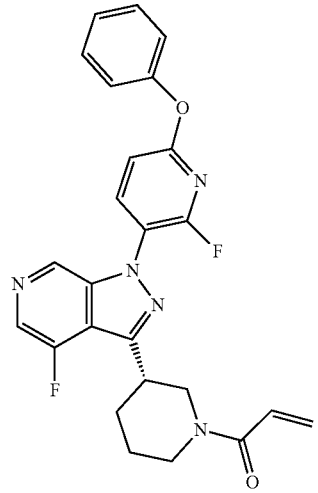

1B or 1A

Synthetic Route:

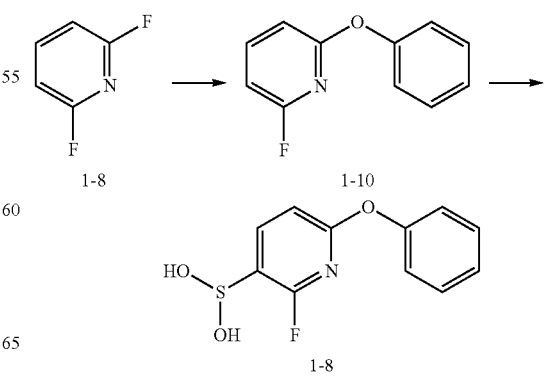

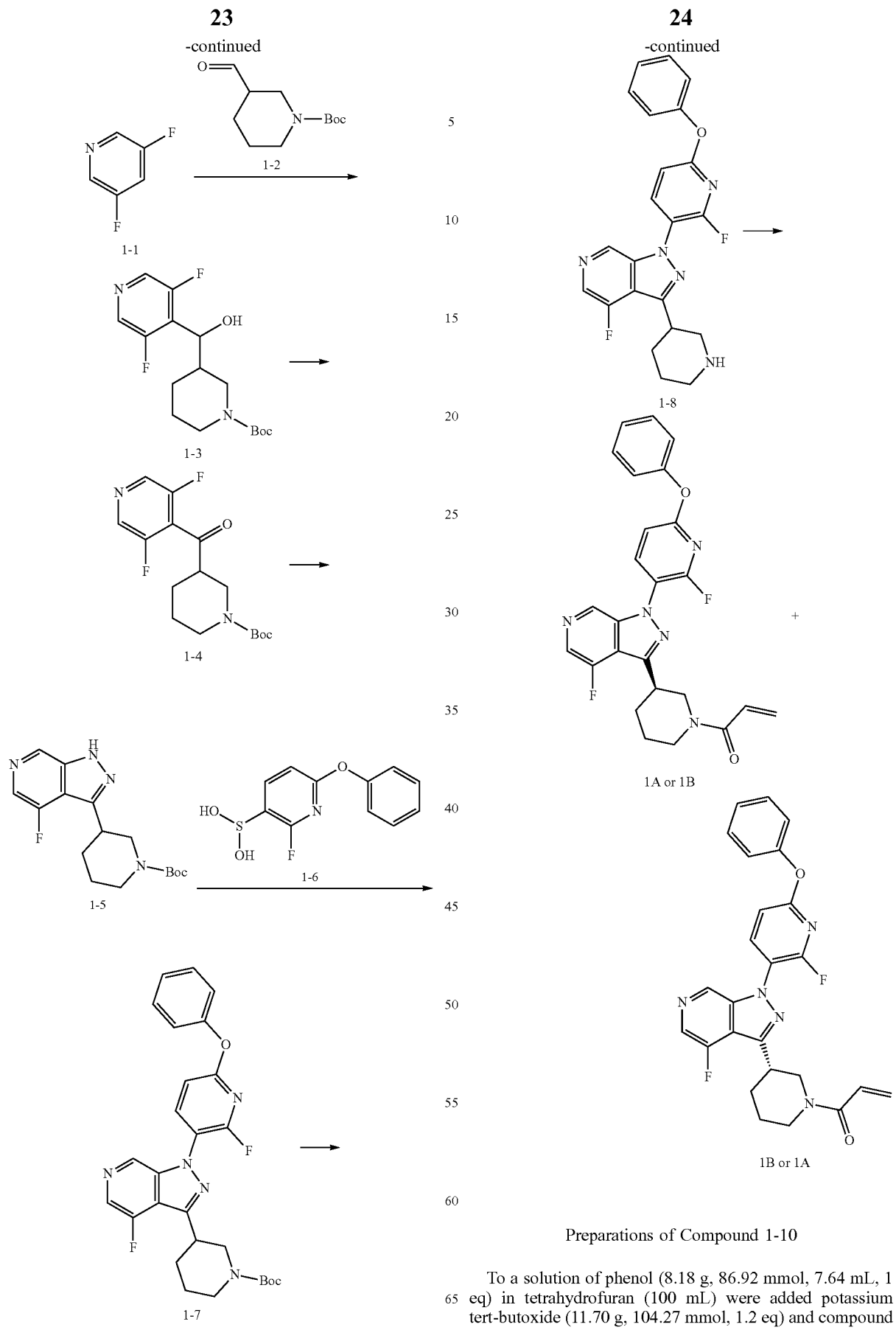
Preparations of Compound 1-10
To a solution of phenol (8.18 g, 86.92 mmol, 7.64 mL, 1 eq) in tetrahydrofuran (100 mL) were added potassium tert-butoxide (11.70 g, 104.27 mmol, 1.2 eq) and compound 1-9 (10 g, 86.90 mmol, 7.94 mL, 1 eq). The resulting reaction solution was reacted at room temperature (30° C.) for 6 hours. The reaction solution was slowly poured into water (150 mL), and extracted with ethyl acetate (100 mL*3). The organic phase was washed successively with 1 N aqueous sodium hydroxide solution (150 mL) and saturated brine (200 mL), dried over anhydrous sodium sulfate and filtered. The filtrate was concentrated under reduced pressure, and then the residue was separated and purified by column chromatography to obtain compound 1-10. $^1$HNMR (400 MHz, DMSO-d$_6$) δ 8.02 (q, J=8.0 Hz, 1H), 7.50-7.41 (m, 2H), 7.31-7.24 (m, 1H), 7.21-7.14 (m, 2H), 6.90 (ddd, J=1.8, 7.8, 14.2 Hz, 2H). LCMS: MS (ESI) m/z (M+H)$^+$: 190.3.

Preparations of Compound 1-6

At −78° C., under nitrogen protection, to a solution of compound 1-10 (0.67 g, 3.54 mmol, 1 eq) in anhydrous tetrahydrofuran (15 mL) was added dropwise n-butyllithium (2.5 M, 1.6 mL, 1.13 eq). The resulting reaction solution was reacted at −78° C. for 1 hour. Then triisopropyl borate (866 mg, 4.60 mmol, 1.06 mL, 1.3 eq) was added, and the mixture was reacted at −78° C. for 1 hour. To the reaction solution was added saturated aqueous ammonium chloride solution (30 mL), and the mixture was extracted with ethyl acetate (20 mL*3). The organic phase was washed with saturated brine (30 mL), dried over anhydrous sodium sulfate and filtered. The filtrate was concentrated under reduced pressure, and then the residue was separated and purified by column chromatography to obtain compound 1-6. $^1$HNMR (400 MHz, DMSO-d$_6$) δ 8.15 (t, J=8.5 Hz, 1H), 7.52-7.39 (m, 2H), 7.32-7.22 (m, 1H), 7.17 (brd, J=7.8 Hz, 2H), 6.87 (dd, J=1.6, 7.9 Hz, 1H), 1.36-1.14 (m, 1H), 0.87-0.55 (m, 1H). LCMS: MS (ESI) m/z (M+H)$^+$: 234.1.

Preparations of Compound 1-3

Preparations of LDA solution: under nitrogen protection, at −78° C., to a solution of diisopropylamine (1.70 g, 16.80 mmol, 2.37 mL, 1.05 eq) in anhydrous tetrahydrofuran (30 mL) was added dropwise n-butyllithium (2.5 M, 7.04 mL, 1.1 eq). The resulting mixture was warmed to 0° C., reacted for 0.5 hours and cooled to −78° C. again for later use.

At −78° C., under nitrogen protection, the above-mentioned LDA solution was added dropwise to a solution of compound 1-1 (1.84 g, 15.99 mmol, 1 eq) in anhydrous tetrahydrofuran (5 mL). The resulting mixture was reacted at −78° C. for 1 hour. To the reaction solution was added dropwise a solution of compound 1-2 (3.41 g, 15.99 mmol, 1 eq) in anhydrous tetrahydrofuran (5 mL). The resulting mixture was gradually warmed to room temperature (24° C.), and reacted for another 16 hours. To the system was added a saturated ammonium chloride solution, and ethyl acetate (20 mL) was added. The liquid was separated and extracted. The organic phase was washed with saturated brine (10 mL), then dried over anhydrous sodium sulfate and filtered. The filtrate was concentrated under reduced pressure, and then the residue was separated and purified by column chromatography to obtain compound 1-3. LCMS: MS (ESI) m/z (M-56+H)$^+$: 272.9.

Preparations of Compounds 1-4

At 0° C., Dess-martin periodinane (7.84 g, 18.47 mmol, 5.72 mL, 1.2 eq) was added to a solution of compound 1-3 (5.07 g, 15.44 mmol, 1 eq) in anhydrous dichloromethane (300 mL). The mixture was gradually warmed to room temperature (26° C.) and reacted for 3 hours. To the system was added a saturated sodium hydrogen carbonate solution (200 mL) and dichloromethane (400 mL). The mixture was filtered, and the filtrate was separated. The organic phase was washed with saturated brine (100 mL), dried over anhydrous sodium sulfate and filtered. The filtrate was concentrated under reduced pressure to obtain compound 1-4. LCMS: MS (ESI) m/z (M-56+H)$^+$: 270.9.

Preparations of Compounds 1-5

To compound 1-4 (5.94 g, 18.20 mmol, 1 eq) in 1,4-dioxane (500 mL) and ethanol (100 mL) were added sodium hydrogen carbonate (1.72 g, 20.51 mmol, 797.50 μL, 1.13 eq) and hydrazine hydrate (2.32 g, 45.35 mmol, 2.25 mL, 2.49 eq). The resulting mixture was heated to 75° C. and reacted for 16 hours. The reaction solution was concentrated under reduced pressure, slurried with dichloromethane/methanol (110 mL, v/v=10/1) and filtered. The filtrate was concentrated under reduced pressure, and then the residue was separated and purified by column chromatography to obtain compound 1-5. LCMS: MS (ESI) m/z (M+H)$^+$: 321.4.

Preparations of Compound 1-7

To a suspension of compound 1-5 (500 mg, 1.56 mmol, 1 eq) and compound 1-6 (600 mg, 2.58 mmol, 1.65 eq) in dichloroethane (20 mL) were added copper acetate (600 mg, 3.30 mmol, 2.12 eq), pyridine (600 mg, 7.59 mmol, 612.24 μL, 4.86 eq) and 4A molecular sieve (500 mg). The resulting mixture was replaced three times with oxygen, and heated to 70° C. and reacted for 40 hours under an oxygen balloon atmosphere. The reaction solution was filtered, and the filtrate was concentrated under reduced pressure. Dichloromethane (100 mL), water (20 mL) and aqueous ammonia (30% purity, 15 mL) were added. The liquid was separated and extracted. The organic phase was dried over anhydrous sodium sulfate and filtered. The filtrate was concentrated under reduced pressure, and then the residue was separated and purified by column chromatography to obtain compound 1-7. LCMS: MS (ESI) m/z (M+H)$^+$: 508.1.

Preparations of Compound 1-8

To compound 1-7 (250 mg, 492.58 μmol, 1 eq) in dichloromethane (4 mL) was added trifluoroacetic acid (1.54 g, 13.51 mmol, 1 mL, 27.42 eq). The resulting mixture was reacted at room temperature (31° C.) for 0.5 hours. The reaction solution was concentrated under reduced pressure to obtain compound 1-8 (crude, trifluoroacetate). LCMS: MS (ESI) m/z (M+H)$^+$: 408.0.

Preparations of Compounds 1A and 1B

To compound 1-8 (200 mg, 383.55 μmol, 1 eq, trifluoroacetate) and sodium carbonate (200 mg, 1.89 mmol, 4.92 eq) in tetrahydrofuran (3 mL) and water (3 mL) was added acryloyl chloride (40 mg, 441.95 μmol, 36.04 μL, 1.15 eq) in tetrahydrofuran (0.1 mL). The resulting mixture was reacted at room temperature (31° C.) for 10 minutes. To the reaction solution was added dichloromethane (50 mL). The liquid was separated and extracted. The organic phase was dried over anhydrous sodium sulfate and filtered. The filtrate was concentrated under reduced pressure, and then the residue was separated and purified successively by column chromatography and high performance liquid chromatography (alkaline); the product was detected by supercritical fluid chromatography (chromatography column: Chiralcel OJ-3 150×4.6 mmI.D, 3 μm; mobile phase: A: supercritical carbon dioxide, B: a solution of 0.05% diethylamine in ethanol; gradient: B, from 5% to 40% over 5 minutes, hold at 40% for 2.5 min, back to 5% and equilibration for 2.5 minutes; flow rate: 2.5 mL/min; column temperature: 35° C.; wavelength: 220 nm) and analyzed as a racemic compound, which was separated to obtain chiral isomer compound 1A and compound 1B with retention time of 5.091 min and 5.687 min respectively.

Compound 1A: $^1$H NMR (400 MHz, DMSO-$d_6$) δ 9.43-9.42 (m, 1H) 8.51-8.49 (m, 1H), 7.51-7.47 (m, 4H), 7.31-7.25 (m, 3H), 6.85-6.83 (m, 1H), 6.13-6.08 (m, 1H), 5.68-5.63 (m, 1H), 4.62-4.58 (m, 1H), 4.32-3.95 (m, 2H), 3.65-3.55 (m, 1H), 2.30-2.20 (m, 1H), 2.05-1.80 (m, 3H), 1.60-1.50 (m, 1H). LCMS: MS (ESI) m/z (M+H)$^+$: 462.2.

Compound 1B: $^1$H NMR (400 MHz, DMSO-$d_6$) δ 9.43-9.41 (m, 1H), 8.49 (s, 1H), 7.51-7.47 (m, 4H), 7.32-7.25 (m, 3H), 6.85-6.83 (m, 1H), 6.12-6.08 (m, 1H), 5.70-5.64 (m, 1H), 4.61-4.58 (m, 1H), 4.29-3.95 (m, 2H), 3.65-3.55 (m, 1H), 2.28-2.20 (m, 1H), 2.05-1.80 (m, 3H), 1.60-1.50 (m, 1H). LCMS: MS (ESI) m/z (M+H)$^+$: 462.0.

Example 2

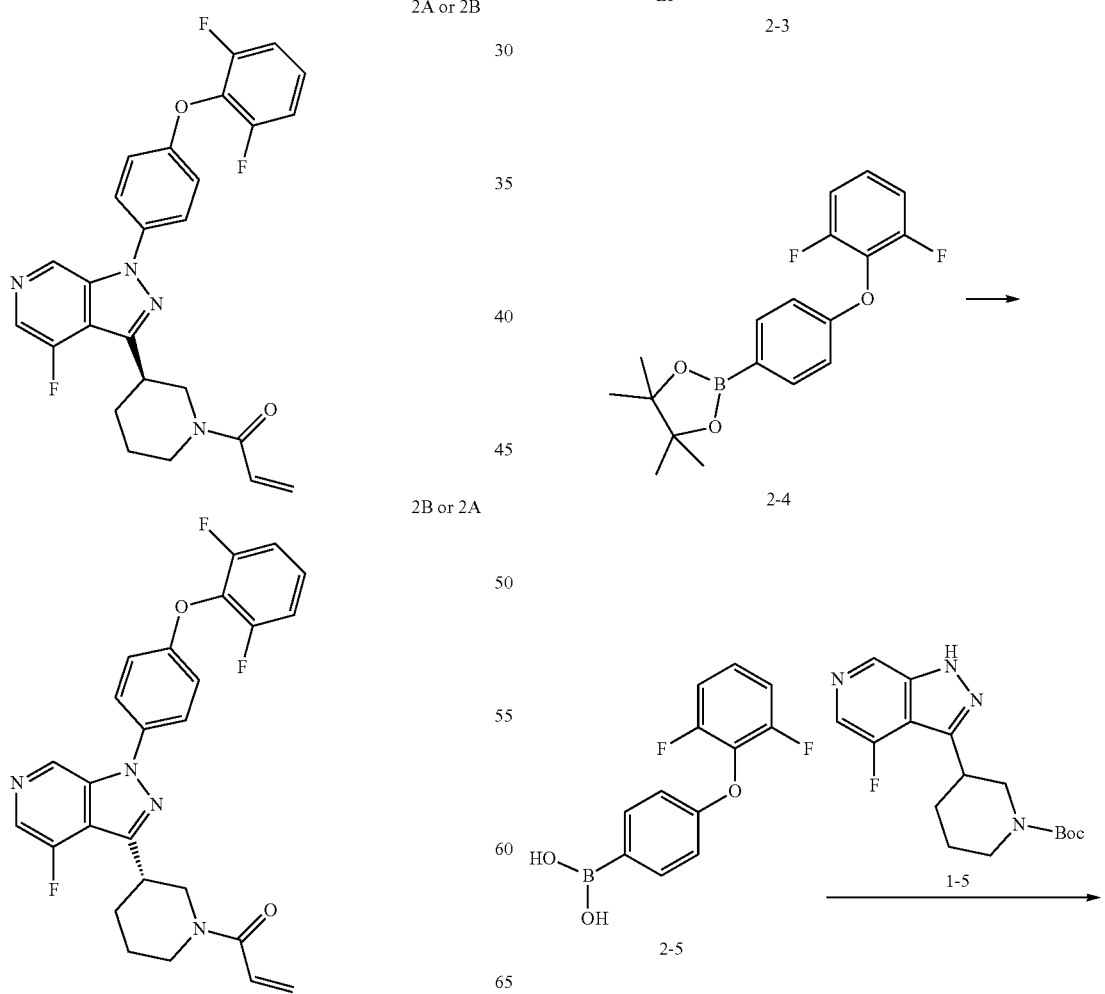

2A or 2B 2B or 2A

Synthetic Route:

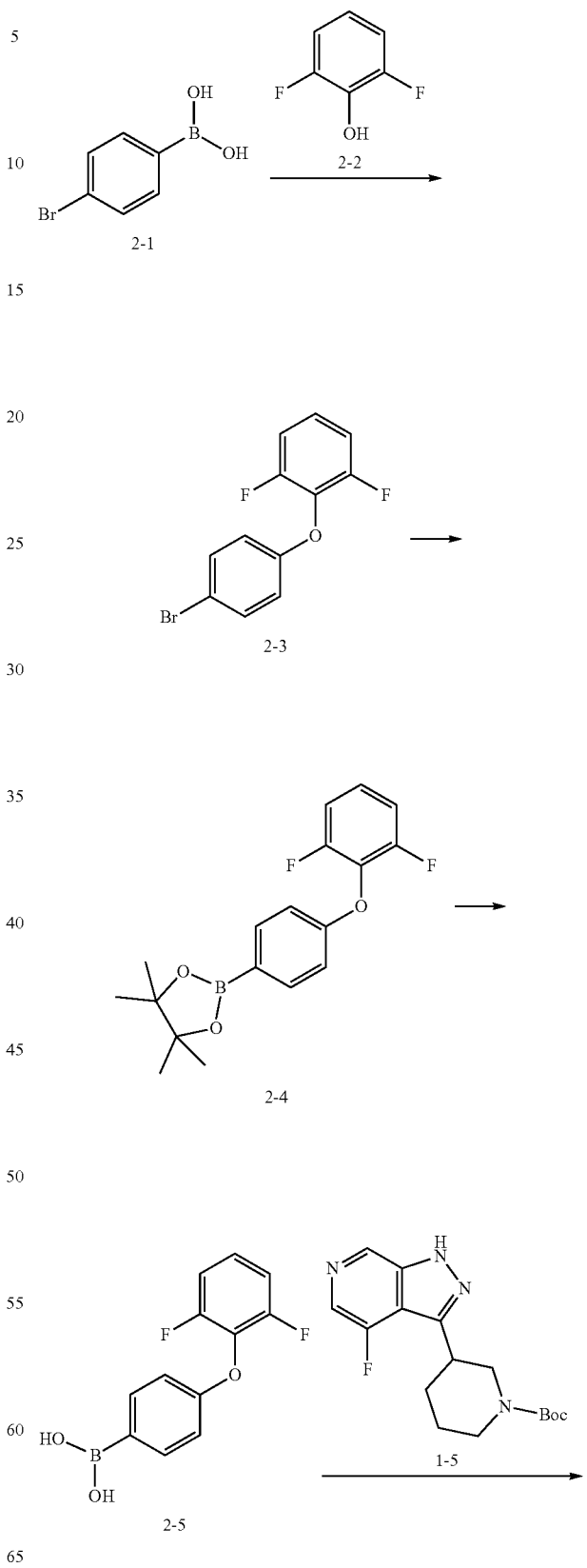

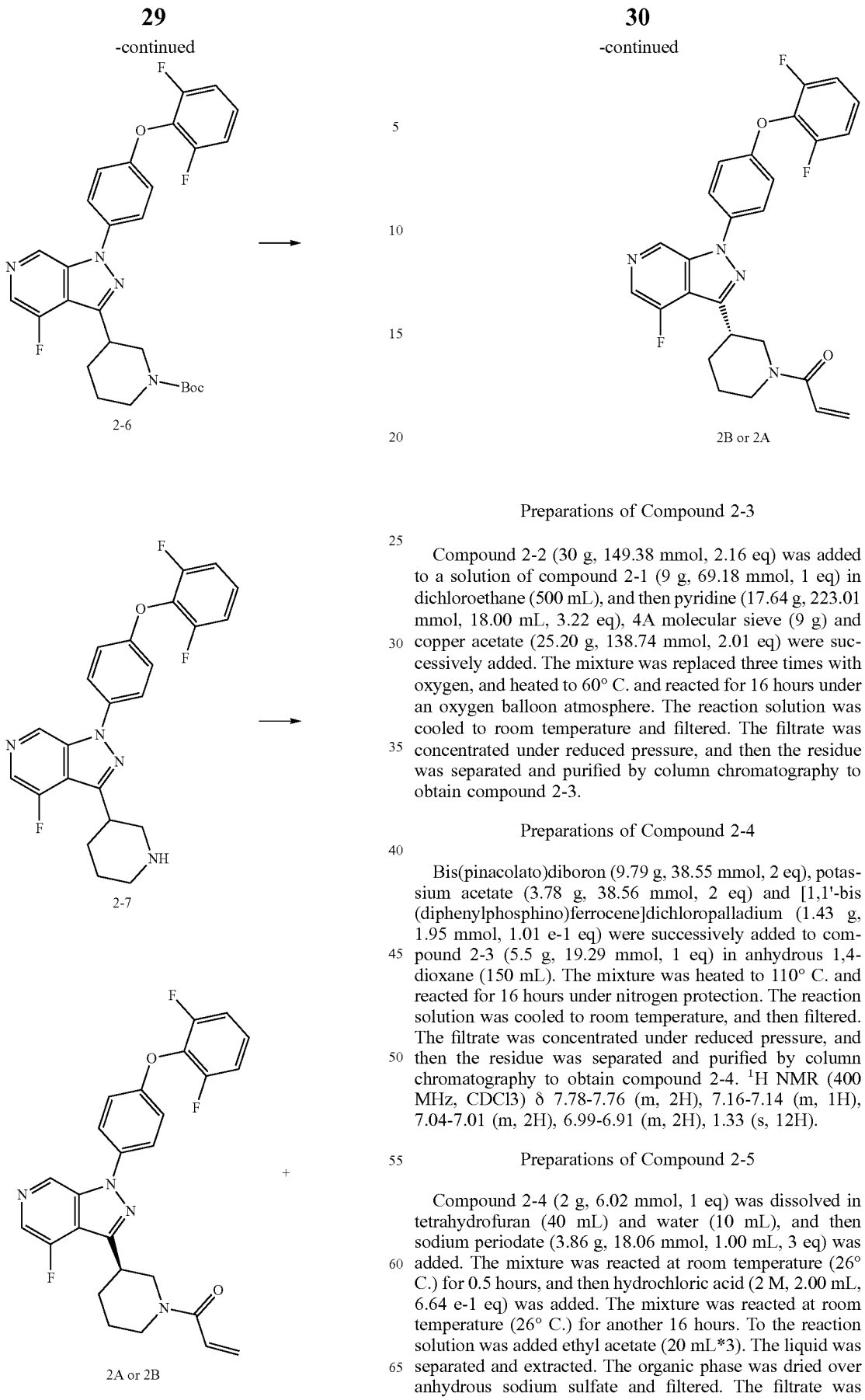

Preparations of Compound 2-3

Compound 2-2 (30 g, 149.38 mmol, 2.16 eq) was added to a solution of compound 2-1 (9 g, 69.18 mmol, 1 eq) in dichloroethane (500 mL), and then pyridine (17.64 g, 223.01 mmol, 18.00 mL, 3.22 eq), 4A molecular sieve (9 g) and copper acetate (25.20 g, 138.74 mmol, 2.01 eq) were successively added. The mixture was replaced three times with oxygen, and heated to 60° C. and reacted for 16 hours under an oxygen balloon atmosphere. The reaction solution was cooled to room temperature and filtered. The filtrate was concentrated under reduced pressure, and then the residue was separated and purified by column chromatography to obtain compound 2-3.

Preparations of Compound 2-4

Bis(pinacolato)diboron (9.79 g, 38.55 mmol, 2 eq), potassium acetate (3.78 g, 38.56 mmol, 2 eq) and [1,1'-bis(diphenylphosphino)ferrocene]dichloropalladium (1.43 g, 1.95 mmol, 1.01 e-1 eq) were successively added to compound 2-3 (5.5 g, 19.29 mmol, 1 eq) in anhydrous 1,4-dioxane (150 mL). The mixture was heated to 110° C. and reacted for 16 hours under nitrogen protection. The reaction solution was cooled to room temperature, and then filtered. The filtrate was concentrated under reduced pressure, and then the residue was separated and purified by column chromatography to obtain compound 2-4. $^1$H NMR (400 MHz, CDCl3) δ 7.78-7.76 (m, 2H), 7.16-7.14 (m, 1H), 7.04-7.01 (m, 2H), 6.99-6.91 (m, 2H), 1.33 (s, 12H).

Preparations of Compound 2-5

Compound 2-4 (2 g, 6.02 mmol, 1 eq) was dissolved in tetrahydrofuran (40 mL) and water (10 mL), and then sodium periodate (3.86 g, 18.06 mmol, 1.00 mL, 3 eq) was added. The mixture was reacted at room temperature (26° C.) for 0.5 hours, and then hydrochloric acid (2 M, 2.00 mL, 6.64 e-1 eq) was added. The mixture was reacted at room temperature (26° C.) for another 16 hours. To the reaction solution was added ethyl acetate (20 mL*3). The liquid was separated and extracted. The organic phase was dried over anhydrous sodium sulfate and filtered. The filtrate was concentrated under reduced pressure, and then the residue was separated and purified by column chromatography to obtain compound 2-5. $^1$H NMR (400 MHz, DMSO-$d_6$) δ 8.16-8.14 (m, 2H), 7.71-7.69 (m, 1H), 7.21-7.18 (m, 1H), 7.07-6.96 (m, 3H).

Preparations of Compound 2-6

Compound 1-5 (400 mg, 1.25 mmol, 1 eq) was added to a solution of compound 2-5 (624.31 mg, 2.50 mmol, 2 eq) in dichloroethane (15 mL), and pyridine (321.44 mg, 4.06 mmol, 328 μL, 3.25 eq), 4A molecular sieve (500 mg) and copper acetate (468 mg, 2.58 mmol, 2.06 eq) were successively added. The mixture was replaced three times with oxygen, and heated to 60° C. and reacted for 16 hours under an oxygen balloon atmosphere. The reaction solution was cooled to room temperature and filtered. The filtrate was concentrated under reduced pressure and dissolved in dichloromethane (5 mL), and water (3 mL) was added. The liquid was separated and extracted. The organic phase was dried over anhydrous sodium sulfate and filtered. The filtrate was concentrated under reduced pressure, and then the residue was separated and purified by column chromatography to obtain compound 2-6. LCMS: MS (ESI) m/z (M+H)$^+$: 525.3.

Preparations of Compound 2-7

Trifluoroacetic acid (4.62 g, 40.52 mmol, 3.00 mL, 70.84 eq) was added to a solution of compound 2-6 (300 mg, 571.94 μmol, 1 eq) in anhydrous dichloromethane (2 mL). The mixture was reacted at room temperature (25° C.) for 0.5 hours. The reaction solution was directly concentrated under reduced pressure. The residue was dissolved by adding dichloromethane (20 mL), and then concentrated under reduced pressure again to obtain compound 2-7 (crude, trifluoroacetate). LCMS: MS (ESI) m/z (M+H)$^+$: 425.0.

Preparations of Compounds 2A and 2B

Compound 2-7 (200 mg, 371.44 μmol, 1 eq, trifluoroacetate) was dissolved in tetrahydrofuran (2 mL) and water (2 mL); sodium carbonate (50.00 mg, 471.74 μmol, 1.27 eq) was added; and a solution of acryloyl chloride (26 mg, 287.27 μmol, 23.42 μL, 7.73 e-1 eq) in anhydrous tetrahydrofuran (0.5 mL) was added dropwise. The mixture was reacted at room temperature (26° C.) for 10 minutes. The reaction solution was adjusted to pH=7 with hydrochloric acid (1 M), and then water (5 mL), dichloromethane (10 mL) and methanol (1 mL) were added. The liquid was separated and extracted. The organic phase was dried over anhydrous sodium sulfate and filtered. The filtrate was concentrated under reduced pressure, and then the residue was separated and purified by high performance liquid chromatography (alkaline); the product was detected by supercritical fluid chromatography (chromatography column: Chiralpak AD-3 50×3 mmI.D, 3 μm; mobile phase: A: supercritical carbon dioxide, B: a solution of 0.05% diethylamine in ethanol; gradient: B, from 5% to 40% over 2.5 minutes, hold at 40% for 0.35 min, back to 5% and equilibration for 0.15 minutes; flow rate: 2.8 mL/min; column temperature: 40° C.; wavelength: 220 nm) and analyzed as a racemic compound, which was separated to obtain chiral isomer compound 2A and compound 2B with retention time of 2.205 min and 2.504 min respectively.

Compound 2A: $^1$HNMR (400 MHz, DMSO-$d_6$) δ 8.94 (s, 1H), 8.21-8.19 (m, 1H), 7.64-7.62 (m, 2H), 7.22-7.05 (m, 5H), 6.69-6.62 (m, 1H), 6.30-6.26 (m, 1H), 5.70-5.65 (m, 1H), 5.01-4.98 (m, 0.5H), 4.65-4.62 (m, 0.5H), 4.33-4.30 (m, 0.5H), 4.09-4.06 (m, 0.5H), 3.52-3.41 (m, 1.5H), 3.20-3.17 (m, 1H), 2.89-2.86 (m, 0.5H), 2.35-2.32 (m, 1H), 2.07-2.04 (m, 2H), 1.96-1.70 (m, 1H). LCMS: MSm/z(M+H)$^+$: 479.5.

Compound 2B: $^1$HNMR (400 MHz, DMSO-$d_6$) δ 8.94 (s, 1H), 8.21-8.19 (m, 1H), 7.64-7.62 (m, 2H), 7.22-7.05 (m, 5H), 6.68-6.62 (m, 1H), 6.30-6.26 (m, 1H), 5.73-5.65 (m, 1H), 5.01-4.98 (m, 0.5H), 4.65-4.62 (m, 0.5H), 4.33-4.30 (m, 0.5H), 4.09-4.06 (m, 0.5H), 3.54-3.41 (m, 1.5H), 3.21-3.17 (m, 1H), 2.92-2.89 (m, 0.5H), 2.35-2.32 (m, 1H), 2.07-2.03 (m, 2H), 1.96-1.70 (m, 11H). LCMS: MSm/z(M+H)$^+$: 479.1.

Example 3

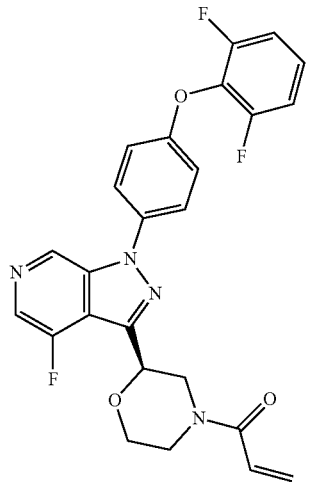

3A or 3B

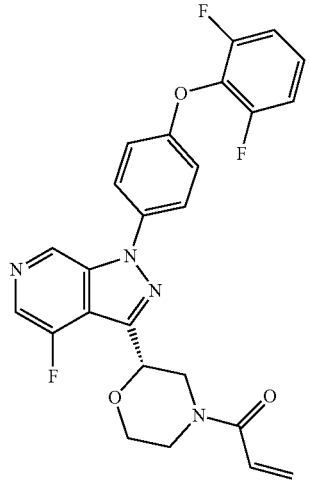

3B or 3A

Synthetic Route:
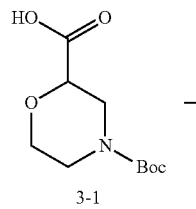
3-1
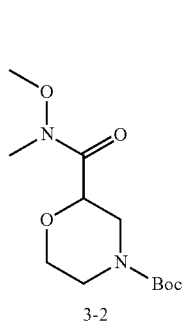
3-2
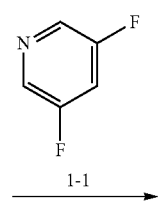
1-1
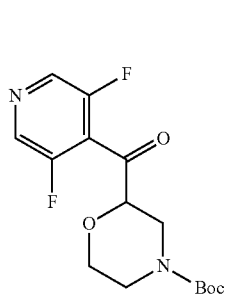
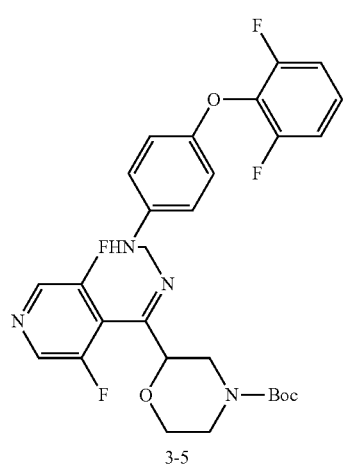
3-4
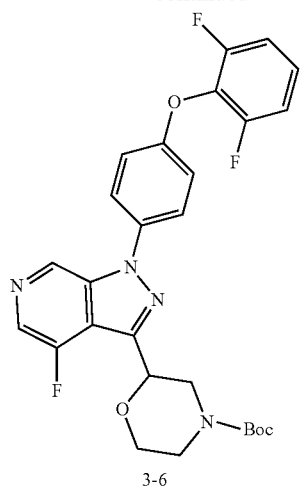
3-6
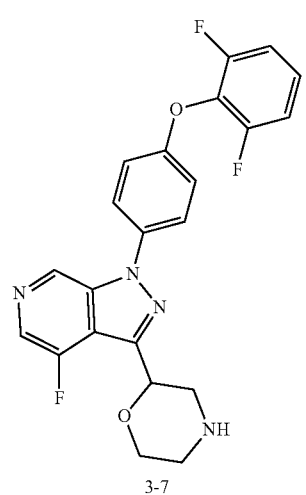
3-7
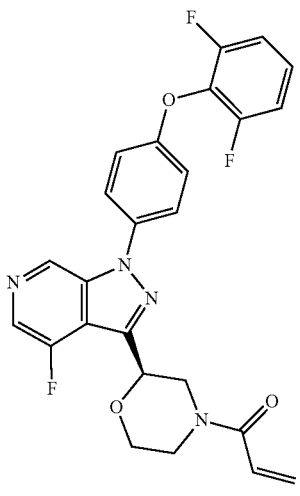
3A or 3B -continued

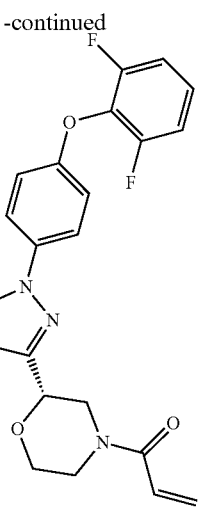

3B or 3A

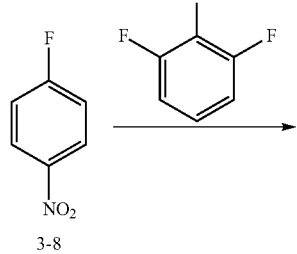

3-8

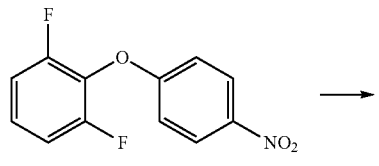

3-9

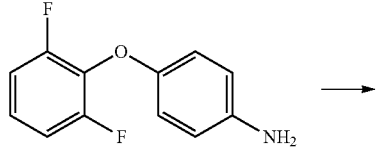

3-10

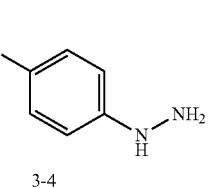

3-4

Preparations of Compound 3-9

Cesium carbonate (46.25 g, 141.95 mmol, 2 eq) was added to a solution of compound 3-8 (10 g, 70.87 mmol, 7.52 mL, 1 eq) and compound 2-2 (11.25 g, 86.48 mmol, 1.22 eq) in anhydrous N,N-dimethylformamide (500 mL). The mixture was reacted at 140° C. for 16 hours. The reaction solution was cooled to room temperature and then concentrated under reduced pressure to remove the solvent; the residue was dissolved by adding ethyl acetate (500 mL), and then water (200 mL) was added. The solution was separated. The organic phase was washed with saturated brine (200 mL), dried over anhydrous sodium sulfate and filtered. The filtrate was concentrated under reduced pressure, and then the residue was separated and purified by column chromatography to obtain compound 3-9.

Preparations of Compound 3-10

Wet palladium carbon (4.5 g, 10% purity) was added to compound 3-9 (9 g, 35.83 mmol, 1 eq) in anhydrous methanol (250 mL). The mixture was replaced three times with hydrogen and reacted at room temperature (15° C.) under a hydrogen balloon atmosphere for 3 hours. The reaction solution was filtered (through celite), and the filtrate was concentrated under reduced pressure to obtain compound 3-10. LCMS: MS (ESI) m/z (M+H)$^+$: 221.7.

Preparations of Compound 3-4

Hydrochloric acid (600 mL, concentrated hydrochloric acid) was added to compound 3-10 (19 g, 85.89 mmol, 1 eq), and the mixture was cooled to 0° C. A solution of sodium nitrite (11.85 g, 171.79 mmol, 2 eq) in water (200 mL) was added dropwise to the above-mentioned reaction solution. The mixture was reacted at 0° C. for 1 hour, and a mixture of stannous chloride dihydrate (79.47 g, 352.17 mmol, 4.1 eq) and hydrochloric acid (200 mL, concentrated hydrochloric acid) was added dropwise. After the dropwise addition was complete, the mixture was reacted at 0° C. for 3 hours. The reaction solution was adjusted to pH=12 with sodium hydroxide (6 M), and dichloromethane (2000 mL) was added. The liquid was separated. The organic phase was washed with saturated brine, dried over anhydrous sodium sulfate and filtered. The filtrate was concentrated under reduced pressure to obtain compound 3-4. $^1$HNMR (400 MHz, CDCl$_3$) δ 7.27 (s, 1H), 7.11-7.00 (m, 2H), 6.98-6.90 (m, 2H), 6.88-6.76 (m, 2H), 5.08 (s, 1H), 3.56 (s, 2H).

Preparations of Compound 3-2

To a solution of compound 3-1 (10 g, 43.24 mmol, 1 eq) in dichloromethane (120 mL) was added N,N'-carbonyldiimidazole (7.71 g, 47.57 mmol, 1.1 eq). The resulting reaction solution was reacted at 10° C. for 1 hour, and N,O-dimethyl hydroxylamine hydrochloride (4.72 g, 48.37 mmol, 1.12 eq) was added. The resulting reaction solution was reacted at 10° C. for 16 hours. To the reaction solution were added dichloromethane (100 mL) and water (60 mL). The liquid was separated and extracted. The organic phase was washed successively with 1 N hydrochloric acid aqueous solution (50 mL), 1 N sodium hydroxide aqueous solution (50 mL) and saturated brine (80 mL), dried over anhydrous sodium sulfate and filtered. The filtrate was concentrated under reduced pressure to obtain compound 3-2. LCMS: MS (ESI) m/z (M-56+H)$^+$: 218.9.

Preparations of Compound 3-3

Preparations of LDA solution: at −78° C., under nitrogen protection, to a solution of diisopropylamine (1.49 g, 14.74 mmol, 2.08 mL, 1.62 eq) in anhydrous tetrahydrofuran (30 mL) was added dropwise n-butyllithium (2.5 M, 6.0 mL, 1.65 eq). The resulting mixture was warmed to 0° C., reacted for 0.5 hours and cooled to −78° C. again for later use.

At −78° C., under nitrogen protection, to the above-mentioned LDA solution was added dropwise a solution of compound 1-1 (2.5 g, 9.11 mmol, 1 eq) and 3-2 (1.26 g, 10.94 mmol, 2.98 mL, 1.2 eq) in anhydrous tetrahydrofuran (20 mL). The resulting mixture was gradually warmed to room temperature (15° C.), and reacted for another 16 hours. The reaction was quenched by adding saturated ammonium chloride (100 mL). Then most of the solvent of the mixed solution was subjected to rotary evaporation under reduced pressure, and the liquid was separated and extracted with ethyl acetate (150 mL). The organic phase was washed with saturated brine (150 mL), dried over anhydrous sodium sulfate and filtered. The filtrate was concentrated under reduced pressure, and then the residue was separated and purified by column chromatography to obtain compound 3-3. LCMS: MS (ESI) m/z (M+H)$^+$: 328.9.

Preparations of Compound 3-5

At 10° C., a mixed solution of compound 3-3 (270 mg, 822.39 μmol, 1 eq), compound 3-4 (540.00 mg, 2.29 mmol, 2.78 eq), acetic acid (2.10 g, 34.97 mmol, 2 mL, 42.52 eq) and ethanol (10 mL) was reacted for 1 hour. The reaction solution was concentrated under reduced pressure to obtain compound 3-5. LCMS: MS (ESI) m/z (M-56+H)$^+$: 491.0.

Preparations of Compound 3-6

To a microwave tube were added compound 3-5 (720 mg, 1.32 mmol, 1 eq), cesium carbonate (1.29 g, 3.96 mmol, 3 eq) and N,N-dimethylformamide (1.5 mL). The resulting reaction solution was heated to 150° C. and reacted for 30 minutes under microwave. The reaction solution was filtered. The filtrate was concentrated under reduced pressure, and then the residue was separated and purified by column chromatography to obtain compound 3-6. LCMS: MS (ESI) m/z (M+H)$^+$: 527.1.

Preparations of Compound 3-7

To a solution of compound 3-6 (0.4 g, 759.73 μmol, 1 eq) in dichloromethane (8 mL) was added trifluoroacetic acid (3.08 g, 27.01 mmol, 2 mL, 35.56 eq). The resulting reaction solution was reacted at 10° C. for 0.5 hours. The reaction solution was concentrated under reduced pressure to obtain compound 3-7 (crude, trifluoroacetate). LCMS: MS (ESI) m/z (M+H)$^+$: 427.0.

Preparations of Compounds 3A and 3B

To a solution of compound 3-7 (420 mg, 985.01 μmol, 1 eq, trifluoroacetate) in tetrahydrofuran (8 mL) were added sodium carbonate (521 mg, 4.92 mmol, 4.99 eq) and water (4 mL); then a solution of acryloyl chloride (180 mg, 1.99 mmol, 162.16 μL, 2.02 eq) in tetrahydrofuran (0.2 mL) was added dropwise. The resulting reaction solution was reacted at 10° C. for 0.5 hours. To the reaction solution were added dichloromethane/methanol (50 mL, 10/1) and water (50 mL). The liquid was separated. The organic phase was washed with saturated brine (50 mL), dried over anhydrous sodium sulfate and filtered. The filtrate was concentrated under reduced pressure, and then the residue was separated and purified by column chromatography; the product was detected by supercritical fluid chromatography (chromatography column: Chiralpak AD-3 50×4.6 mm I.D, 3 μm; mobile phase: A: supercritical carbon dioxide, B: a solution of 0.05% diethylamine in ethanol; gradient: B, from 5% to 40% over 2 minutes, hold at 40% for 1.2 min, back to 5% and equilibration for 0.8 minutes; flow rate: 4 mL/min; column temperature: 35° C.; wavelength: 220 nm) and analyzed as a racemic compound, which was separated to obtain chiral isomer compound 3A and compound 3B with retention time of 1.979 min and 2.083 min respectively.

Compound 3A: $^1$HNMR (400 MHz, DMSO-d$_6$) δ 9.11 (brs, 1H), 8.37 (brs, 1H), 7.85 (brd, J=8.5 Hz, 2H), 7.51-7.33 (m, 3H), 7.22 (brd, J=8.5 Hz, 2H), 6.88 (brdd, J=10.3, 16.6 Hz, 1H), 6.18 (brt, J=13.3 Hz, 1H), 5.83-5.66 (m, 1H), 5.10-4.91 (m, 1H), 4.67 (brd, J=13.1 Hz, 0.5H), 4.42-4.21 (m, 1H), 4.18-3.92 (m, 2H), 3.86-3.63 (m, 2H), 3.09 (brs, 0.5H). LCMS: MS (ESI) m/z (M+H)$^+$: 481.1.

Compound 3B: $^1$HNMR (400 MHz, DMSO-d$_6$) δ 9.15 (brs, 1H), 8.41 (brs, 1H), 7.89 (brd, J=8.8 Hz, 2H), 7.54-7.37 (m, 3H), 7.25 (brd, J=8.8 Hz, 2H), 6.91 (brdd, J=10.7, 16.4 Hz, 1H), 6.29-6.14 (m, 1H), 5.85-5.68 (m, 1H), 5.12-4.95 (m, 1H), 4.71 (brd, J=12.8 Hz, 0.5H), 4.46-4.23 (m, 1H), 4.22-3.91 (m, 2H), 3.90-3.67 (m, 2H), 3.14 (brd, J=10.8 Hz, 0.5H). LCMS: MS (ESI) m/z (M+H)$^+$: 481.1.

Example 4

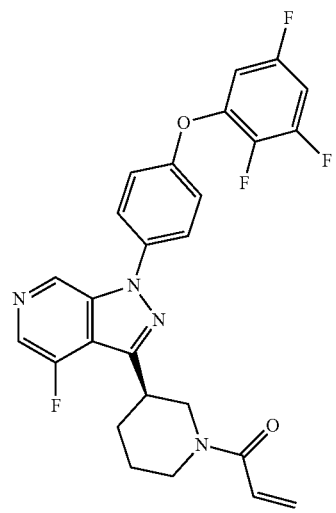

4A or 4B

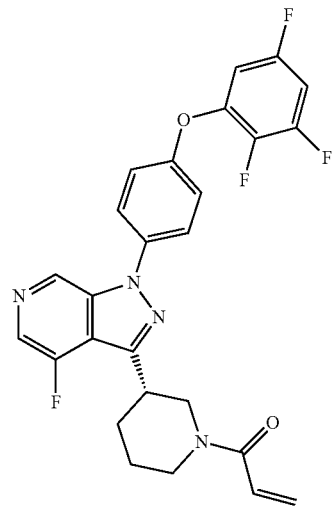

4B or 4A

Synthetic Route:
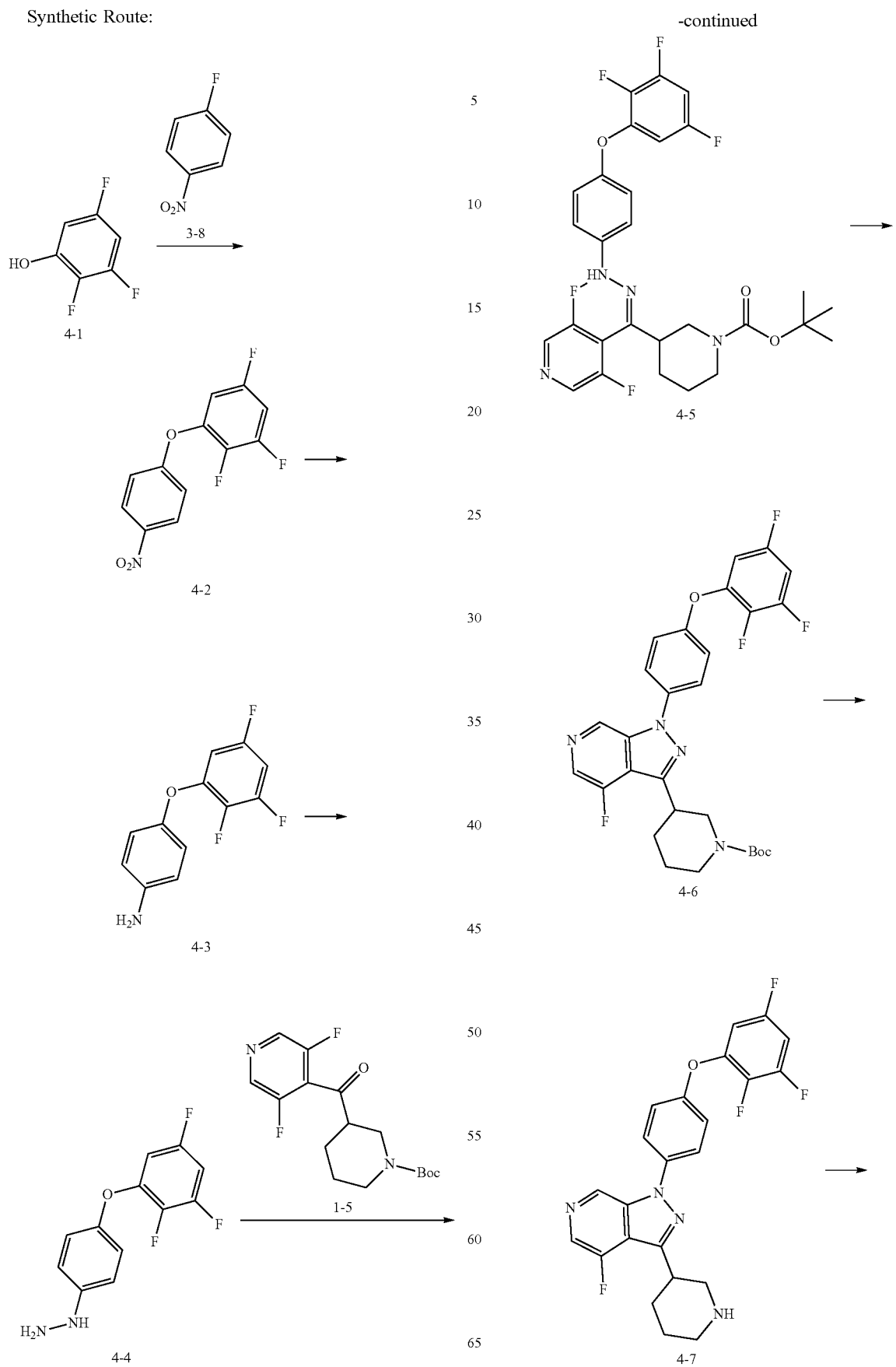

-continued

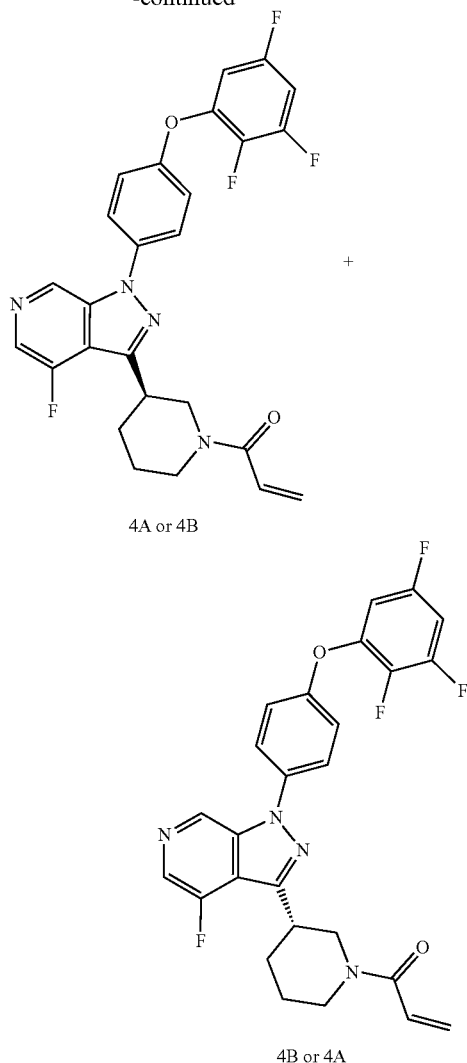

4A or 4B

+

4B or 4A

Preparations of Compound 4-2

Cesium carbonate (14.78 g, 45.36 mmol, 2 eq) was added to a solution of compound 3-8 (3.2 g, 22.68 mmol, 2.41 mL, 1 eq) and compound 4-1 (4 g, 27.01 mmol, 1.19 eq) in anhydrous N,N-dimethylformamide (100 mL). The mixture was reacted at 100° C. for 2.5 hours. The reaction solution was cooled to room temperature, and concentrated under reduced pressure. The residue was dissolved by adding ethyl acetate (200 mL), and then water (200 mL) was added. The solution was separated. The organic phase was washed with saturated brine (100 mL), then dried over anhydrous sodium sulfate and filtered. The filtrate was concentrated under reduced pressure to obtain compound 4-2.

Preparations of Compound 4-3

Wet palladium carbon (4 g, 10% purity) was added to compound 4-2 (4 g, 14.86 mmol, 1 eq) in anhydrous methanol (150 mL). The mixture was replaced three times with hydrogen, and reacted at room temperature (10° C.) under a hydrogen balloon atmosphere (15 psi) for 16 hours. The reaction solution was filtered (through celite), and the filtrate was concentrated under reduced pressure to obtain compound 4-3. LCMS: MS (ESI) m/z (M+H)$^+$: 239.8.

Preparations of Compound 4-4

Hydrochloric acid (200 mL, concentrated hydrochloric acid) was added to compound 4-3 (6.5 g, 27.17 mmol, 1 eq), and the mixture was cooled to 0° C. A solution of sodium nitrite (3.75 g, 54.35 mmol, 2 eq) in water (70 mL) was added dropwise to the above-mentioned reaction solution. The mixture was reacted at 0° C. for 1 hour, then a mixture of tin chloride dihydrate (24.53 g, 108.70 mmol, 4 eq) and hydrochloric acid (70 mL, concentrated hydrochloric acid) was added dropwise. After the dropwise addition was complete, the mixture was reacted at 0° C. for 3 hours, gradually warmed to room temperature (10° C.) and reacted for another 16 hours. The pH was adjusted to about 12 with sodium hydroxide (6 M), and dichloromethane (500 mL*3) was added. The liquid was separated and extracted. The organic phase was washed with saturated brine, dried over anhydrous sodium sulfate and filtered. The filtrate was concentrated under reduced pressure to obtain compound 4-4. LCMS: MS (ESI) m/z (M+H)$^+$: 255.0.

Preparations of Compound 4-5

To a solution of compound 1-5 (0.5 g, 1.53 mmol, 1 eq) and compound 4-4 (1.00 g, 3.93 mmol, 2.57 eq) in ethanol (15 mL) was added acetic acid (3.15 g, 52.38 mmol, 3 μmL, 34.24 eq). The mixture was reacted at room temperature (20° C.) for 16 hours. The reaction solution was concentrated under reduced pressure to obtain compound 4-5. LCMS: MS (ESI) m/z (M-56+H)$^+$: 507.3.

Preparations of Compound 4-6

To a solution of compound 4-5 (1.59 g, 2.83 mmol, 1 eq) in N,N-dimethylformamide (20 mL) was added cesium carbonate (2.76 g, 8.48 mmol, 3 eq). The mixture was warmed to 135° C. and reacted for 1.5 hours. The reaction solution was filtered (through celite), and the filter cake was washed with N,N-dimethylformamide (20 mL). The combined filtrate was concentrated under reduced pressure, and then the residue was separated and purified by column chromatography to obtain compound 4-6. LCMS: MS (ESI) m/z (M+H)$^+$: 543.3.

Preparations of Compound 4-7

To a solution of compound 4-6 (110 mg, 196.92 μmol, 1 eq) in dichloromethane (4 mL) was added trifluoroacetic acid (1.54 g, 13.51 mmol, 1 mL, 68.59 eq). The mixture was reacted at room temperature (20° C.) for 0.5 hours. The reaction solution was concentrated under reduced pressure to obtain compound 4-7 (crude, trifluoroacetate). LCMS: MS (ESI) m/z (M+H)$^+$: 443.1.

Preparations of Compounds 4A and 4B

To a solution of compound 4-7 (677 mg, 1.22 mmol, 1 eq, trifluoroacetate) in tetrahydrofuran (10 mL) and water (10 mL) was added sodium carbonate (1 g, 9.43 mmol, 7.75 eq), and to the reaction solution was added dropwise a solution of acryloyl chloride (63 mg, 696.07 μmol, 56.76 μL, 5.72 e-1 eq) in tetrahydrofuran (1 mL). The mixture was reacted at room temperature (25° C.) for 1 hour and supplemented with a solution of acyl chloride (35 mg, 386.71 μmol, 31.53 μL, 3.18 e-1 eq) in tetrahydrofuran (1 mL), and the resulting solution was reacted at room temperature (25° C.) for another 0.5 hours. The reaction solution was adjusted to pH of about 5 with 1 N hydrochloric acid, and extracted with dichloromethane (10 mL*3). The combined organic phase was dried over anhydrous sodium sulfate and filtered. The filtrate was concentrated under reduced pressure, and then the residue was separated and purified by column chromatography; the product was detected by supercritical fluid chromatography (chromatography column: Chiralpak AD-3 50×4.6 mmI.D, 3 μm; mobile phase: A: supercritical carbon dioxide, B: a solution of 0.05% diethylamine in methanol; gradient: B, from 5% to 40% over 2 minutes, hold at 40% for 1.2 min, back to 5% and equilibration for 0.8 minutes; flow rate: 4 mL/min; column temperature: 35° C.; wavelength: 220 nm) and analyzed as a racemic compound, which was separated to obtain chiral isomer compound 4A and compound 4B with retention time of 2.134 min and 2.518 min respectively.

Compound 4A: $^1$HNMR (400 MHz, DMSO-$d_6$) δ 9.11 (s, 1H), 8.34 (s, 1H), 7.87 (d, J=8.8 Hz, 2H), 7.48-7.39 (m, 1H), 7.35 (d, J=8.8 Hz, 2H), 7.14-7.03 (m, 1H), 6.94-6.75 (m, 1H), 6.09 (t, J=16.3 Hz, 1H), 5.73-5.55 (m, 1H), 4.72 (d, J=12.0 Hz, 0.5H), 4.31 (t, J=14.8 Hz, 1H), 4.08 (d, J=13.3 Hz, 0.5H), 3.55-3.43 (m, 0.5H), 3.32-3.13 (m, 1.5H), 3.13-2.90 (m, 1H), 2.27-2.17 (m, 1H), 2.06-1.81 (m, 2H), 1.65-1.49 (m, 1H). LCMS: MS (ESI) m/z (M+H)$^+$: 497.2.

Compound 4B: $^1$HNMR (400 MHz, DMSO-$d_6$) δ 9.12 (s, 1H), 8.36 (s, 1H), 7.89 (d, J=8.8 Hz, 2H), 7.52-7.40 (m, 1H), 7.37 (d, J=9.0 Hz, 2H), 7.16-7.06 (m, 1H), 6.94-6.74 (m, 1H), 6.10 (t, J=16.6 Hz, 1H), 5.75-5.56 (m, 1H), 4.73 (d, J=11.5 Hz, 0.5H), 4.32 (t, J=15.1 Hz, 1H), 4.10 (d, J=13.1 Hz, 0.5H), 3.58-3.44 (m, 0.5H), 3.32-3.13 (m, 1.5H), 3.15-2.92 (m, 1H), 2.27-2.17 (m, 1H), 2.09-1.82 (m, 2H), 1.65-1.49 (m, 1H). LCMS: MS (ESI) m/z (M+H)$^+$: 497.2.

Example 5

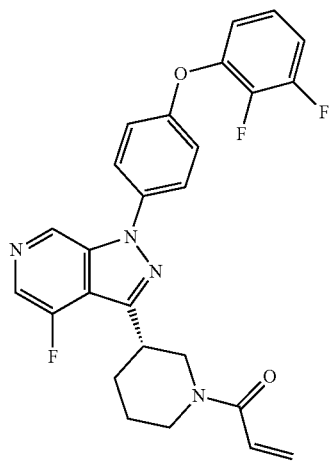

5A or 5B

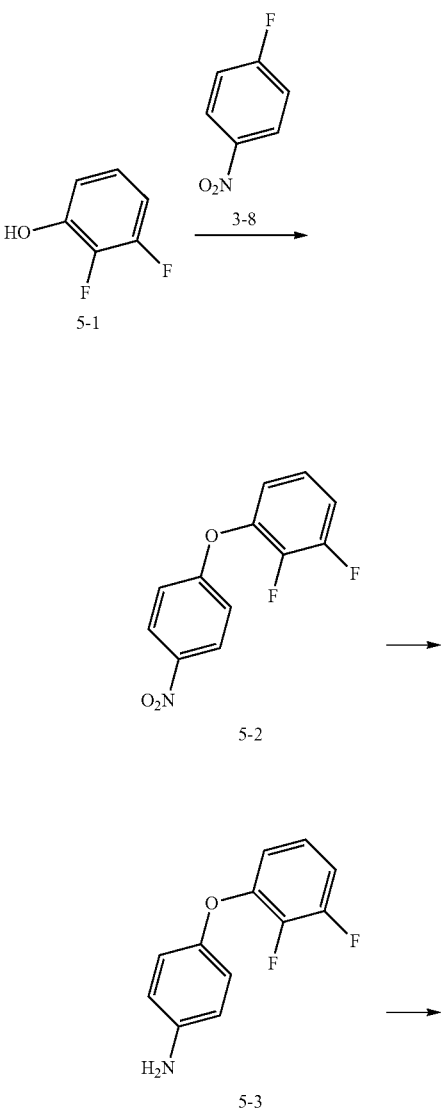

5B or 5A

Synthetic Route:

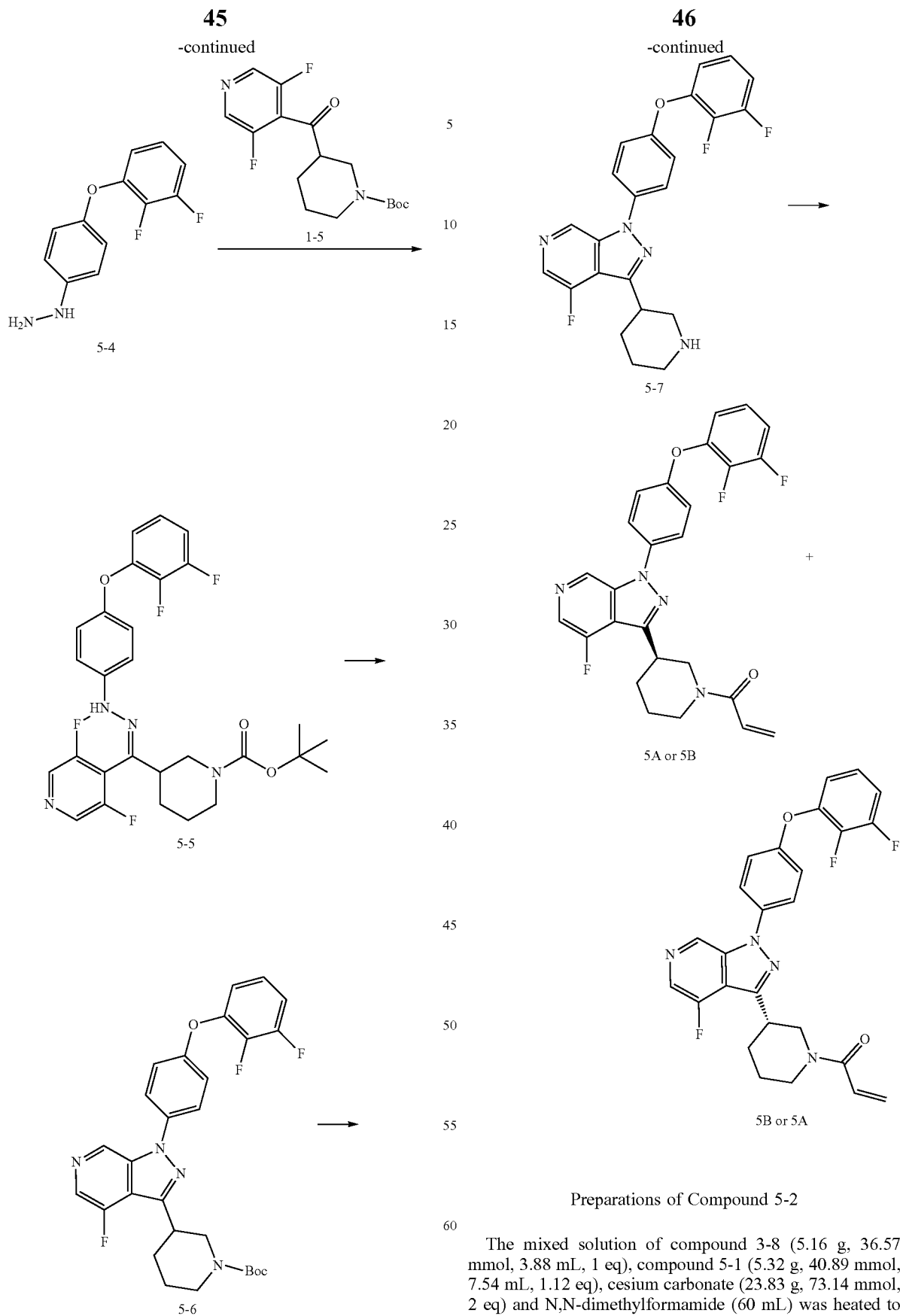
Preparations of Compound 5-2
The mixed solution of compound 3-8 (5.16 g, 36.57 mmol, 3.88 mL, 1 eq), compound 5-1 (5.32 g, 40.89 mmol, 7.54 mL, 1.12 eq), cesium carbonate (23.83 g, 73.14 mmol, 2 eq) and N,N-dimethylformamide (60 mL) was heated to 80° C. and stirred for 2 hours. The reaction solution was concentrated under reduced pressure, and then the residue was separated and purified by column chromatography to obtain compound 5-2. $^1$HNMR (400 MHz, CDCl$_3$) δ 8.24-8.26 (m, 2H), 6.99-7.17 (m, 5H).

Preparations of Compound 5-3

To a solution of compound 5-2 (4.5 g, 17.92 mmol, 1 eq) in methanol (60 mL) was added wet palladium carbon (2.3 g, 10% purity). The mixture was replaced three times with hydrogen, and then stirred at 15° C. under a hydrogen balloon atmosphere for 16 hours. The reaction solution was filtered (through celite). The filtrate was concentrated under reduced pressure, and then the residue was separated and purified by column chromatography to obtain compound 5-3. $^1$HNMR (400 MHz, CDCl$_3$) δ 6.79-6.83 (m, 4H), 6.64-6.53 (m, 3H), 3.54 (brs, 2H). LCMS: MS (ESI) m/z (M+H)$^+$: 222.1

Preparations of Compound 5-4

At 0° C., to a solution of compound 5-3 (5.5 g, 24.86 mmol, 1 eq) in hydrochloric acid (150 mL, concentrated hydrochloric acid) was added dropwise a solution of sodium nitrite (3.43 g, 49.73 mmol, 2 eq) in water (50 mL), and the mixture was reacted at 0° C. for 1 hour. Then to the reaction solution was added dropwise a solution of tin chloride dihydrate (23.00 g, 101.94 mmol, 4.1 eq) in hydrochloric acid (50 mL, concentrated hydrochloric acid), and the mixture was reacted at 0° C. for 3 hours. The reaction solution was adjusted to pH of about 13 with sodium hydroxide solution (6 N), and extracted with dichloromethane (200 mL*3). The combined organic phase was dried over anhydrous sodium sulfate and filtered. The filtrate was concentrated under reduced pressure to obtain compound 5-4. LCMS: MS (ESI) m/z (M+H)$^+$: 237.1.

Preparations of Compound 5-5

To a solution of compound 1-5 (500 mg, 1.53 mmol, 1 eq) and compound 5-4 (1.00 g, 4.23 mmol, 2.76 eq) in ethanol (25 mL) was added acetic acid (5.25 g, 87.43 mmol, 5 mL, 57.06 eq), and the mixture was reacted at room temperature (25° C.) for 16 hours. The reaction solution was concentrated under reduced pressure to obtain compound 5-5. LCMS: MS (ESI) m/z (M-56+H)$^+$: 489.1.

Preparations of Compound 5-6

To a solution of compound 5-5 (1.9 g, 3.49 mmol, 1 eq) in N,N-dimethylformamide (30 mL) was added cesium carbonate (3.45 g, 10.57 mmol, 3.03 eq). The mixture was warmed to 135° C. and reacted for 1 hour. The reaction solution was filtered (through celite), and the filter cake was washed with N,N-dimethylformamide (30 mL). The filtrate was concentrated under reduced pressure, and then the residue was separated and purified by column chromatography to obtain compound 5-6. LCMS: MS (ESI) m/z (M+H)$^+$: 525.3.

Preparations of Compound 5-7

To compound 5-6 (585 mg, 1.12 mmol, 1 eq) in dichloromethane (16 mL) was added dropwise trifluoroacetic acid (6.16 g, 54.02 mmol, 4 mL, 48.44 eq), and the mixture was reacted at room temperature (30° C.) for 0.5 hours. The reaction solution was concentrated under reduced pressure to obtain compound 5-7 (crude, trifluoroacetate). LCMS: MS (ESI) m/z (M+H)$^+$: 425.2.

Preparations of Compounds 5A and 5B

To a solution of compound 5-7 (1.36 g, 2.53 mmol, 1 eq, trifluoroacetate) in tetrahydrofuran (10 mL) and water (10 mL) was added sodium carbonate (1.15 g, 10.85 mmol, 4.30 eq), and to the reaction solution was added dropwise a solution of acryloyl chloride (130 mg, 1.44 mmol, 117.12 µL, 5.69 e-1 eq) in tetrahydrofuran (1 mL). The mixture was reacted at room temperature (25° C.) for 1 hour. The reaction solution was adjusted to pH of about 5 with 1 N hydrochloric acid, and extracted with dichloromethane (10 mL*3). The combined organic phase was dried over anhydrous sodium sulfate and filtered. The filtrate was concentrated under reduced pressure, and then the residue was separated and purified by column chromatography; the product was detected by supercritical fluid chromatography (chromatography column: Cellulose 2 150×4.6 mmI.D, 5 m; mobile phase: A: supercritical carbon dioxide, B: a solution of 0.05% diethylamine in ethanol; gradient: B, from 5% to 40% over 5 minutes, hold at 40% for 2.5 min, back to 5% and equilibration for 2.5 minutes; flow rate: 2.5 mL/min; column temperature: 35° C.; wavelength: 220 nm) and analyzed as a racemic compound, which was separated to obtain chiral isomer compound 5A and compound 5B with retention time of 6.616 min and 6.971 min respectively.

Compound 5A: $^1$HNMR (400 MHz, DMSO-d$_6$) δ 9.09 (s, 1H), 8.33 (s, 1H), 7.85 (d, J=9.0 Hz, 2H), 7.39-7.22 (m, 4H), 7.16-7.05 (m, 1H), 6.92-6.76 (m, 1H), 6.09 (t, J=16.1 Hz, 1H), 5.72-5.57 (m, 1H), 4.72 (d, J=12.3 Hz, 0.5H), 4.31 (t, J=13.7 Hz, 1H), 4.17-4.00 (m, 0.5H), 3.53-3.44 (m, 0.5H), 3.33-3.14 (m, 1.5H), 3.12-3.02 (m, 0.5H), 3.01-2.89 (m, 0.5H), 2.27-2.16 (m, 1H), 2.05-1.80 (m, 2H), 1.66-1.46 (m, 1H). LCMS: MS (ESI) m/z (M+H)$^+$: 479.2.

Compound 5B: $^1$HNMR (400 MHz, DMSO-d$_6$) δ 9.09 (s, 1H), 8.33 (s, 1H), 7.85 (d, J=8.8 Hz, 2H), 7.40-7.23 (m, 4H), 7.14-7.04 (m, 1H), 6.94-6.75 (m, 1H), 6.10 (t, J=16.1 Hz, 1H), 5.72-5.52 (m, 1H), 4.73 (d, J=12.5 Hz, 0.5H), 4.32 (t, J=12.7 Hz, 1H), 4.09 (d, J=13.1 Hz, 0.5H), 3.57-3.44 (m, 0.5H), 3.33-3.15 (m, 1.5H), 3.12-3.03 (m, 0.5H), 3.03-2.88 (m, 0.5H), 2.27-2.16 (m, 1H), 2.05-1.79 (m, 2H), 1.68-1.49 (m, 1H). LCMS: MS (ESI) m/z (M+H)$^+$: 479.2.

Example 6

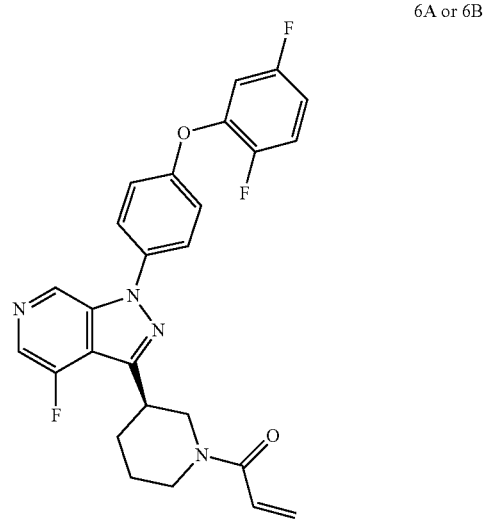

6A or 6B

-continued
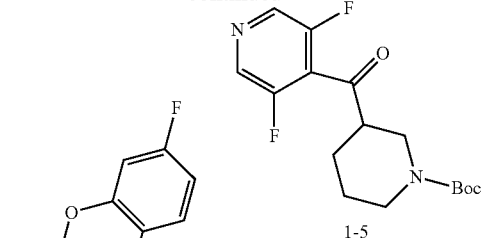
Synthetic Route:
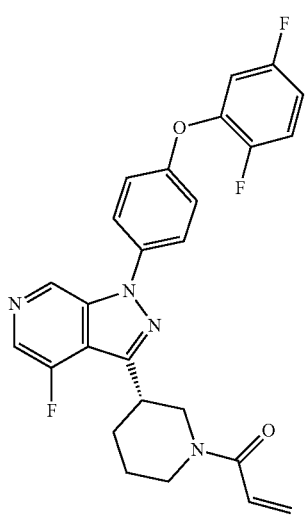
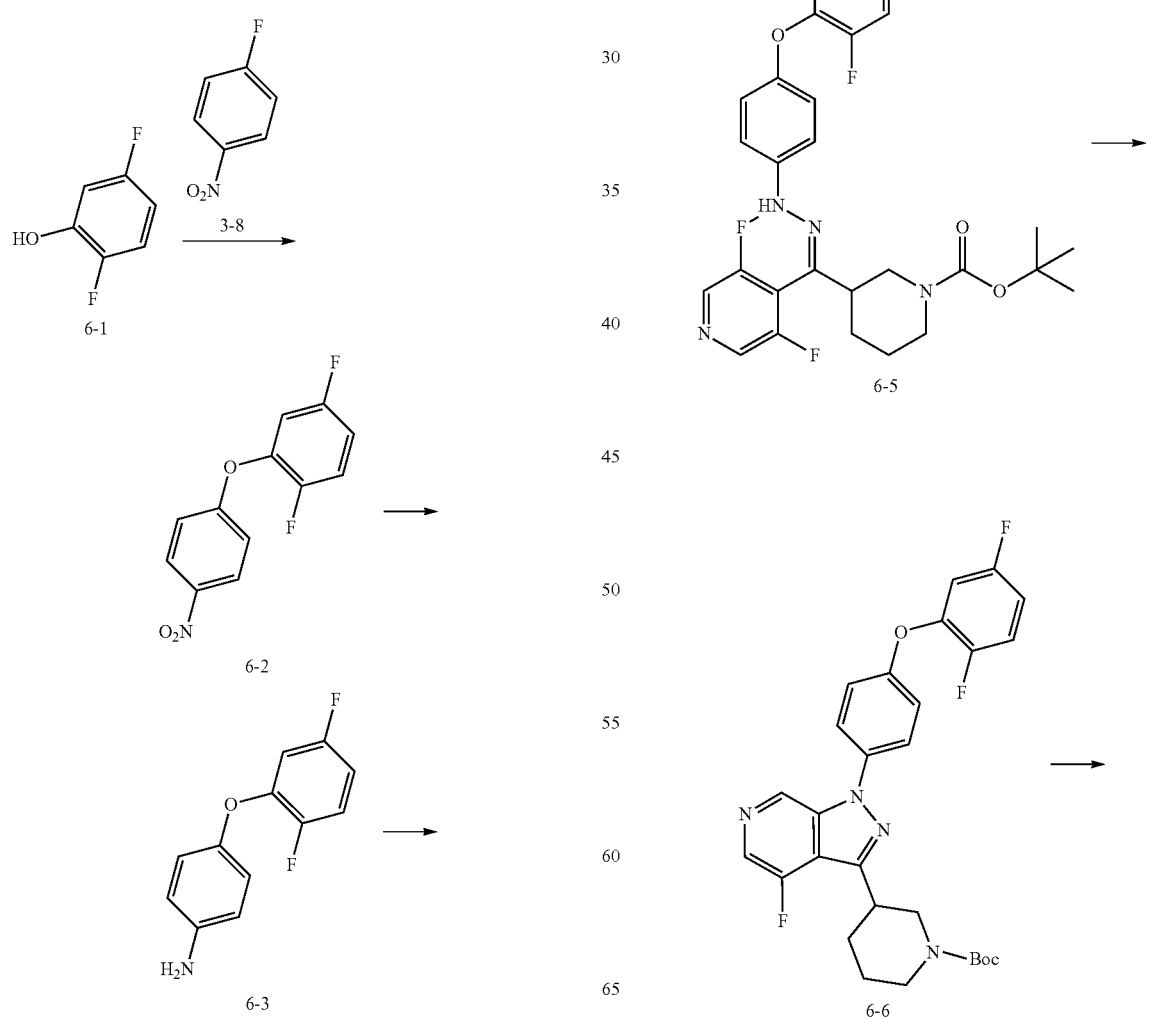

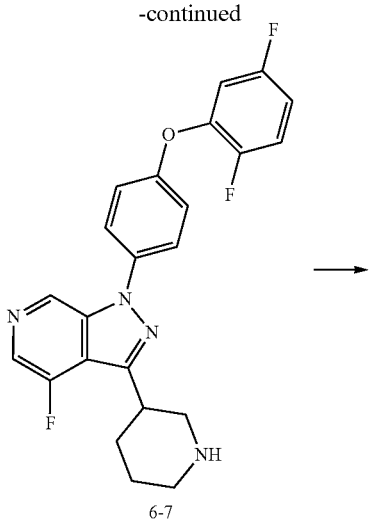

6-7

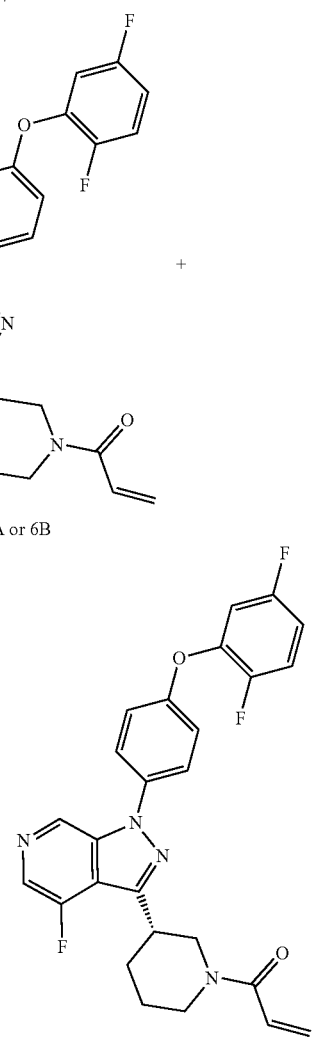

6A or 6B

+

6B or 6A

Preparations of Compound 6-2

To a solution of compound 6-1 (19 g, 134.66 mmol, 14.29 mL, 1 eq) and compound 3-8 (20.22 g, 155.43 mmol, 1.15 eq) in N,N-dimethylformamide (400 mL) was added cesium carbonate (84 g, 257.81 mmol, 1.91 eq). The mixture was warmed to 80° C. and reacted for 16 hours. The reaction solution was filtered (through celite), and the filter cake was washed with N,N-dimethylformamide (30 mL). The combined filtrate was poured to 2 L of water under reaction. Then the mixture was reacted at room temperature (20° C.) for another 10 minutes, and then filtered. The filter cake was washed with water (20 mL*5), and the obtained filter cake was dissolved in 150 mL of dichloromethane. The solution was washed with 20 mL of saturated brine. The organic phase was dried over anhydrous sodium sulfate and filtered. The filtrate was concentrated under reduced pressure to obtain compound 6-2. $^1$HNMR (400 MHz, DMSO-$d_6$) δ 8.28-8.25 (m, 2H), 7.56-7.52 (m, 1H), 7.45-7.30 (m, 1H), 7.25-7.19 (m, 3H).

Preparations of Compound 6-3

To a solution of compound 6-2 (8 g, 31.85 mmol, 1 eq) in methanol (90 mL) was added wet palladium carbon (4 g, 10% purity). The mixture was replaced three times with hydrogen, and reacted at room temperature (25° C.) under a hydrogen balloon (15 psi) atmosphere for 16 hours. The reaction solution was filtered (through celite), and the filtrate was concentrated under reduced pressure to obtain compound 6-3. LCMS: MS (ESI) m/z (M+H)$^+$: 222.1.

Preparations of Compound 6-4

At 0° C., to a solution of compound 6-3 (6.00 g, 27.12 mmol, 1 eq) in hydrochloric acid (180 mL, concentrated hydrochloric acid) was added dropwise a solution of sodium nitrite (3.74 g, 54.25 mmol, 2 eq) in water (60 mL), and the mixture was reacted at 0° C. for 1 hour. Then to the reaction solution was added dropwise a solution of tin chloride dihydrate (25.09 g, 111.21 mmol, 4.1 eq) in hydrochloric acid (60 mL, concentrated hydrochloric acid), and the mixture was reacted at 0° C. for 5 hours. The reaction solution was adjusted to pH of about 12 with 6 N sodium hydroxide solution and extracted with dichloromethane (150 mL*3). The combined organic phase was dried over anhydrous sodium sulfate and filtered. The filtrate was concentrated under reduced pressure to obtain compound 6-4. LCMS: MS (ESI) m/z (M+H)$^+$: 237.1.

Preparations of Compound 6-5

To a solution of compound 1-5 (500 mg, 1.53 mmol, 1 eq) and compound 6-4 (1 g, 4.23 mmol, 2.76 eq) in ethanol (20 mL) was added acetic acid (4.20 g, 69.94 mmol, 4 mL, 45.65 eq). The mixture was reacted at room temperature (25° C.) for 16 hours. The reaction solution was concentrated under reduced pressure to obtain compound 6-5. LCMS: MS (ESI) m/z (M-56+H)$^+$: 489.3.

Preparations of Compound 6-6

To a solution of compound 6-5 (800 mg, 1.47 mmol, 1 eq) in N,N-dimethylformamide (15 mL) was added cesium carbonate (1.5 g, 4.60 mmol, 3.13 eq). The mixture was warmed to 150° C. under microwave and reacted for 0.5 hours. The reaction solution was filtered (through celite), and the filter cake was washed with N,N-dimethylformamide (20 mL). The combined filtrate was concentrated under reduced pressure, and then the residue was separated and purified by column chromatography to obtain compound 6-6. LCMS: MS (ESI) m/z (M+H)+: 525.3.

Preparations of Compound 6-7

To a solution of compound 6-6 (330 mg, 629.13 μmol, 1 eq) in dichloromethane (8 mL) was added trifluoroacetic acid (3.08 g, 27.01 mmol, 2 mL, 42.94 eq). The mixture was reacted at room temperature (25° C.) for 0.5 hours. The reaction solution was concentrated under reduced pressure to obtain compound 6-7 (crude, trifluoroacetate). LCMS: MS (ESI) m/z (M+H)+: 425.2.

Preparations of Compounds 6A and 6B

To a solution of compound 6-7 (780 mg, 1.45 mmol, 1 eq, trifluoroacetate) in tetrahydrofuran (10 mL) and water (10 mL) was added sodium carbonate (1.19 g, 11.23 mmol, 7.75 eq), and a solution of acryloyl chloride (70 mg, 773.41 μmol, 63.06 μL, 5.34 e-1 eq) in tetrahydrofuran (1 mL) was added dropwise. The mixture was reacted at room temperature (25° C.) for 1 hour. The reaction solution was adjusted to pH of about 5 with 1 N hydrochloric acid, and extracted with dichloromethane (10 mL*3). The combined organic phase was dried over anhydrous sodium sulfate and filtered. The filtrate was concentrated under reduced pressure, and then the residue was separated and purified by column chromatography; the product was detected by supercritical fluid chromatography (chromatography column: Chiralpak IG-3 50×4.6 mmI.D, 3 μm; mobile phase: A: supercritical carbon dioxide, B: a solution of 0.05% diethylamine in ethanol; gradient: B, from 5% to 40% over 2 minutes, hold at 40% for 1.2 min, back to 5% and equilibration for 0.8 minutes; flow rate: 4 mL/min; column temperature: 35° C.; wavelength: 220 nm) and analyzed as a racemic compound, which was separated to obtain chiral isomer compound 6A and compound 6B with retention time of 2.820 min and 3.128 min respectively.

Compound 6A: $^1$HNMR (400 MHz, DMSO-$d_6$) δ 9.10 (s, 1H), 8.34 (s, 1H), 7.85 (d, J=8.8 Hz, 2H), 7.56-7.47 (m, 1H), 7.31-7.20 (m, 3H), 7.19-7.11 (m, 1H), 6.92-6.74 (m, 1H), 6.09 (t, J=16.2 Hz, 1H), 5.75-5.58 (m, 1H), 4.73 (d, J=12.0 Hz, 0.5H), 4.41-4.23 (m, 1H), 4.09 (d, J=13.1 Hz, 0.5H), 3.54-3.44 (m, 0.5H), 3.34-2.90 (m, 2.5H), 2.30-2.16 (m, 1H), 2.07-1.81 (m, 2H), 1.67-1.48 (m, 1H). LCMS: MS (ESI) m/z (M+H)+: 479.3.

Compound 6B: $^1$HNMR (400 MHz, DMSO-$d_6$) δ 9.10 (s, 1H), 8.35 (s, 1H), 7.86 (d, J=8.8 Hz, 2H), 7.56-7.47 (m, 1H), 7.35-7.23 (m, 3H), 7.19-7.11 (m, 1H), 6.93-6.74 (m, 1H), 6.10 (t, J=16.3 Hz, 1H), 5.76-5.57 (m, 1H,) 4.73 (d, J=12.5 Hz, 0.5H), 4.32 (t, J=14.1 Hz, 1H), 4.10 (d, J=13.1 Hz, 0.5H), 3.55-3.45 (m, 0.5H), 3.34-2.88 (m, 2.5H), 2.30-2.16 (m, 1H), 2.07-1.82 (m, 2H), 1.68-1.46 (m, 1H). LCMS: MS (ESI) m/z (M+H)+: 479.3.

Reference Example 7

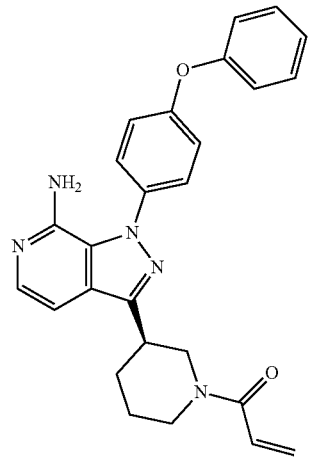

7A or 7B

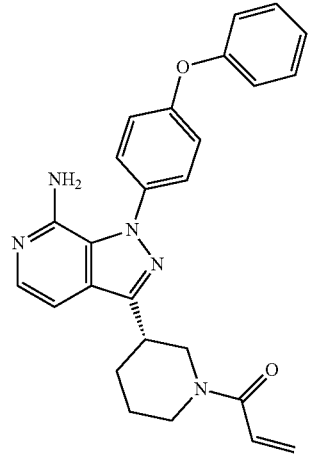

7B or 7A

Synthetic Route:

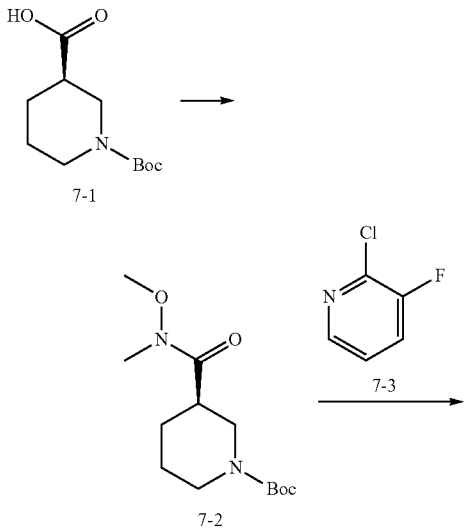

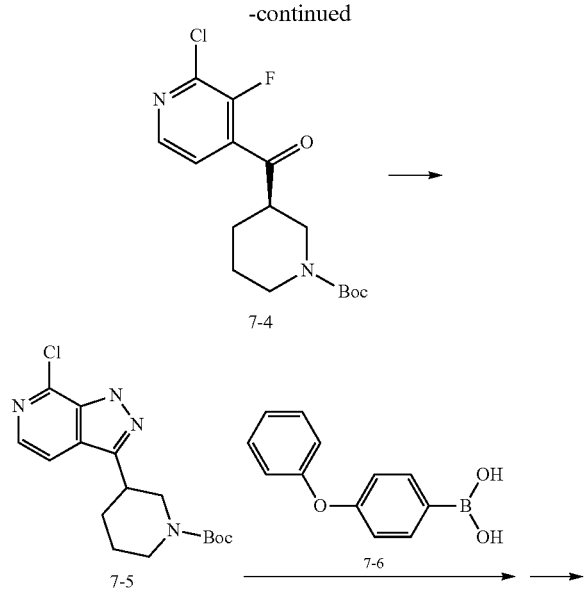
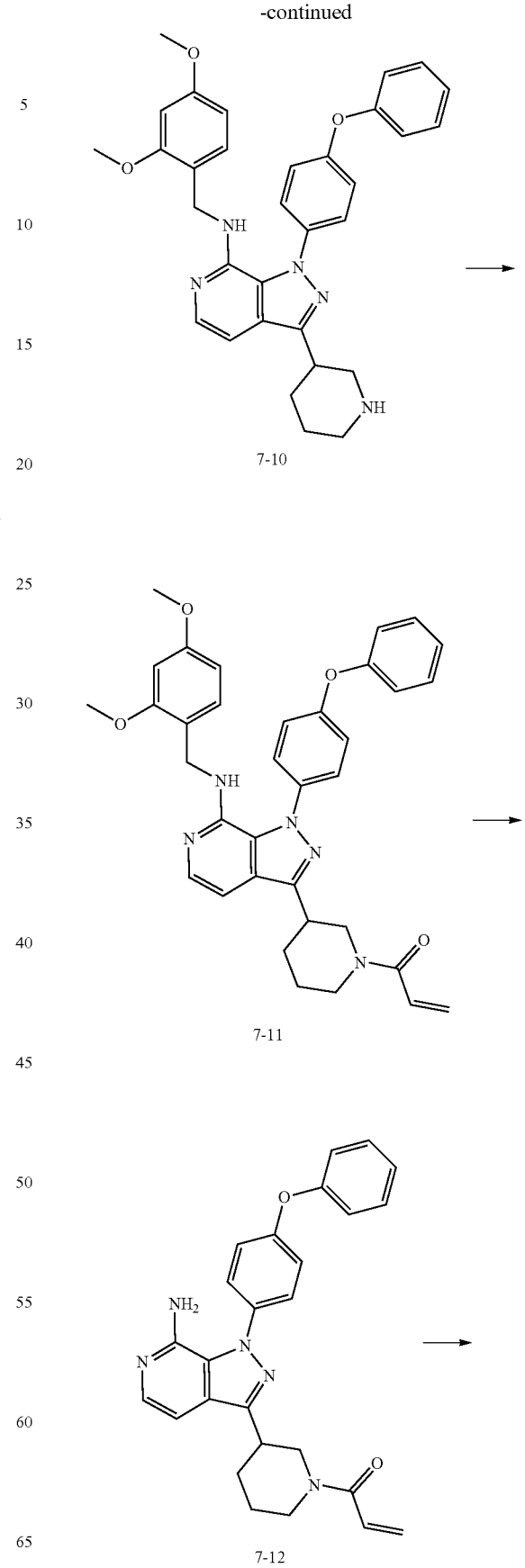

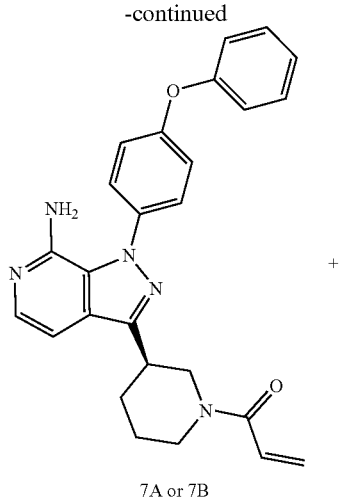

7A or 7B

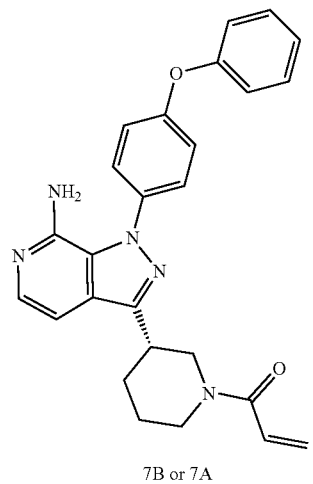

7B or 7A

Preparations of Compound 7-2

To compound 7-1 (6.47 g, 28.22 mmol, 1 eq) in dichloromethane (90 mL) was added N,N'-carbonyldiimidazole (5.64 g, 34.78 mmol, 1.23 eq). The resulting mixture was stirred at room temperature (25° C.) for 1 hours, and N,O-dimethyl hydroxylamine hydrochloride (3.12 g, 31.99 mmol, 1.13 eq) was added. The mixture was stirred at room temperature (25° C.) for 16 hours. The reaction solution was washed successively with 1 M hydrochloric acid (80 ml) and saturated sodium hydrogen carbonate solution (80 ml), and the liquid was separated and extracted. The organic phase was washed with saturated brine (50 ml), then dried over anhydrous sodium sulfate, filtered, and concentrated to dryness under reduced pressure to obtain compound 7-2. LCMS: MS (ESI) m/z (M-56+H)$^+$: 217.1.

Preparations of Compound 7-4

At −65° C., under nitrogen protection, to a solution of compound 7-3 (3.81 g, 28.96 mmol, 1.54 eq) in THF (40 mL) was added dropwise n-butyllithium (2.5 M, 11 mL, 1.46 eq), and the mixture was reacted at −65° C. for 1 hour. Then a solution of compound 7-2 (5.12 g, 18.80 mmol, 1 eq) in THF (40 mL) was added, and the mixture was reacted at −65° C. for 2 hours, slowly warmed to normal temperature (25° C.) and then reacted for another 16 hours. The reaction was quenched by adding dropwise saturated ammonium chloride solution (15 ml) to the reaction solution, and concentrated to dryness under reduced pressure. The resulting concentrated residue was diluted with ethyl acetate (150 ml) and water (40 ml), and the liquid was separated and extracted. The organic phase was dried over anhydrous sodium sulfate and filtered. The filtrate was concentrated to dryness under reduced pressure, and then the residue was purified by a silica gel column to obtain compound 7-4. LCMS: MS (ESI) m/z (M-56+H)$^+$: 287.1.

Preparations of Compound 7-5

To the mixed solution of compound 7-4 (7.43 g, 21.67 mmol, 1 eq) in 1,4-dioxane (56 mL) and ethanol (28 mL) were successively added sodium carbonate (1.83 g, 21.78 mmol, 847.22 uL, 1 eq) and hydrazine hydrate (1.51 g, 25.57 mmol, 1.46 mL, 1.18 eq, purity 85%). The mixture was heated to 70° C. and reacted for 16 hours. The reaction solution was concentrated to dryness, and then the residue was purified by a silica gel column to obtain compound 7-5. LCMS: MS (ESI) m/z (M+H)$^+$: 337.2.

Preparations of Compound 7-7

To a suspension of dichloromethane (100 mL) and 4A molecular sieve (4.86 g) were added compound 7-5 (4.78 g, 14.19 mmol, 1 eq), compound 7-6 (4.88 g, 22.80 mmol, 1.61 eq), copper acetate (3.78 g) and pyridine (2.25 g, 28.50 mmol, 2.3 mL, 2.01 eq). The resulting mixture was replaced three times with oxygen, heated to 60° C. and reacted for 16 hours under an oxygen balloon atmosphere, supplemented with 7-6 (4.88 g, 22.80 mmol, 1.61 eq) and then reacted at 60° C. under an oxygen atmosphere for another 16 hours. The reaction solution was filtered, and the filtrate was concentrated to dryness under reduced pressure. Ethyl acetate (200 ml) and water (60 ml) were added, and the liquid was separated and extracted. The organic phase was dried over anhydrous sodium sulfate and filtered. The filtrate was concentrated to dryness under reduced pressure. Then the residue was purified by a silica gel column to obtain compound 7-7. LCMS: MS (ESI) m/z (M+H)$^+$: 505.3.

Preparations of Compound 7-9

To compound 7-8 (7.77 g, 46.47 mmol, 7 mL, 14.21 eq) were added compound 7-7 (1.65 g, 3.27 mmol, 1 eq) and sodium carbonate (540 mg, 6.43 mmol, 250.00 uL, 1.97 eq). The mixture was reacted at 130° C. for 16 hours. To the reaction solution was added water (40 ml), and the liquid was separated and extracted with ethyl acetate (50 ml*2). The combined organic phase was dried over anhydrous sodium sulfate and filtered. The filtrate was concentrated to dryness under reduced pressure. Then the residue was purified by a silica gel column to obtain compound 7-9. LCMS: MS (ESI) m/z (M+H)$^+$: 636.5.

Preparations of Compound 7-10

To compound 7-9 (805 mg, 1.27 mmol, 1 eq) were added dichloromethane (35 mL) and trifluoroacetic acid (5.39 g, 47.27 mmol, 3.50 mL, 37.33 eq). The mixture was reacted at 0° C. for 0.5 hours. The reaction solution was concentrated to dryness under reduced pressure to obtain compound 7-10 (crude, trifluoroacetate). LCMS: MS (ESI) m/z (M+H)$^+$: 536.4.

Preparations of Compound 7-11

At 0° C., to a solution of compound 7-10 (1.15 g, 1.77 mmol, 1 eq, TFA) and sodium carbonate (625 mg, 5.90 mmol, 3.33 eq) in tetrahydrofuran (30 mL) and water (30 mL) was added dropwise acryloyl chloride (307 mg, 3.39 mmol, 276.58 uL, 1.92 eq). The mixture was reacted at 0° C. for another 0.5 hours. To the reaction solution were added dichloromethane (50 ml) and water (20 ml), and the liquid was separated and extracted. The organic phase was dried over anhydrous sodium sulfate and filtered. The filtrate was concentrated to dryness under reduced pressure to obtain compound 7-11. LCMS: MS (ESI) m/z (M+H)$^+$: 590.4.

Preparations of Compound 7-12

To TFA (15 mL) was added compound 7-11 (511.16 mg, 866.84 μmol, 1 eq). The mixture was stirred at 60° C. for 2 hours. The reaction solution was concentrated to dryness under reduced pressure, and then the residue was separated and purified successively by column chromatography and high performance liquid chromatography to obtain compound 7-12. LCMS: MS (ESI) m/z (M+H)$^+$: 440.3.

Preparations of Compounds 7A and 7B

Compound 7-12 (44 mg, 100.11 μmol, 1 eq) was detected by SFC (chromatography column: ChiralpakAD-350×4.6 mmI.D., 3 μm; mobile phase: A: supercritical carbon dioxide, B: a solution of 0.05% diethylamine in isopropanol; gradient: 40% of B; flow rate: 4 mL/min; column temperature: 35° C.; wavelength: 220 nm) and showed a non-single configuration. The product was subjected to chiral resolution to obtain compounds 7A and 7B with retention time of 1.199 min and 2.095 min respectively.

Compound 7A: $^1$HNMR (400 MHz, DMSO-d$_6$) δ 7.70-7.68 (m, 1H), 7.52-7.43 (m, 2H), 7.45-7.43 (m, 2H), 7.21-7.16 (m, 5H), 6.86-6.84 (m, 2H), 6.15-6.08 (m, 1H), 5.71-5.68 (m, 2H), 5.02-5.64 (m, 1H), 4.22-4.11 (m, 1H), 3.52-3.44 (m, 1H), 3.24-3.21 (m, 2H), 3.18-2.90 (m, 1H), 2.15-2.11 (m, 1H), 1.93-1.86 (m, 2H), 1.56-1.52 (m, 1H). LCMS: MS (ESI) m/z (M+H)$^+$: 440.3.

Compound 7B: $^1$HNMR (400 MHz, DMSO-d$_6$) δ 7.70-7.68 (m, 1H), 7.52-7.43 (m, 2H), 7.47-7.45 (m, 2H), 7.22-7.15 (m, 5H), 6.87-6.83 (m, 2H), 6.14-6.08 (m, 1H), 5.73-5.69 (m, 2H), 5.02-5.65 (m, 1H), 4.23-4.12 (m, 1H), 3.51-3.44 (m, 1H), 3.24-3.20 (m, 2H), 3.19-2.90 (m, 1H), 2.16-2.13 (m, 1H), 1.94-1.87 (m, 2H), 1.57-1.54 (m, 1H). LCMS: MS (ESI) m/z (M+H)$^+$: 440.2.

Experimental Example 1: BTK Kinase Test

1. Reaction conditions:
buffer conditions: 20 mM HEPES (pH 7.5), 10 mM MgCl$_2$, 1 mM EGTA, 0.02% Brij35, 0.02 mg/mL BSA, 0.1 mm Na$_3$VO$_4$, 2 mm DTT, 1% DMSO.
2. Reaction procedure:
2.1. Preparing an indicator substrate in a freshly prepared reaction buffer
2.2. Delivering the desired cofactor to the above substrate solution
2.3. Delivering the indicated kinase to the substrate solution and gently mixing same
2.4. Delivering the compounds in DMSO to the kinase reaction mixture using acoustic technology (Echo550)
2.5. Initiating the reaction (final concentration of ATP: 5 μM) by delivering $^{33}$P-ATP (final specific activity: 0.01 μci/μL) to the reaction mixture
2.6. Incubating the kinase reaction at room temperature for 120 minutes
2.7. Recording the reaction on P81 ion exchange paper (Whatman #3698-915)
2.8. Washing the filter widely with 0.75% phosphoric acid
2.9. Measuring the radioactive phosphorylated substrate remaining on the filter paper.
3. Data analysis:
the kinase activity data is expressed as the percentage of the remaining kinase activity in a test sample compared to a reaction with a carrier (dimethyl sulfoxide), and IC$_{50}$ values and curve fitting are obtained using Prism4 software (GraphPad).
4. Experimental conclusion: the results are shown in Table 1.

TABLE 1

| BTK kinase inhibitory activity | | | |
|---|---|---|---|
| Compound No. | BTK (IC$_{50}$, nM) | Compound No. | BTK (IC$_{50}$, nM) |
| 2B | 5.27 | 5A | 31.8 |
| 3A | 9.58 | 5B | 2.16 |
| 3B | 2.7 | 6A | 9.58 |
| 4A | 11 | 6B | 140 |
| 4B | 98.1 | | |

Conclusion: the compounds of the present disclosure exhibit a better kinase inhibitory activity, and preferably, the compounds have a strong kinase inhibitory activity (IC$_{50}$<100 nM).

Experimental Example 2: EGFR, ITK and TEC Kinase Test

1. Reaction conditions:
buffer conditions: 20 mM HEPES (pH 7.5), 10 mM MgCl$_2$, 1 mM EGTA, 0.02% Brij35, 0.02 mg/mL BSA, 0.1 mm Na$_3$VO$_4$, 2 mm DTT, 1% DMSO.
2. Reaction procedure:
2.1. Preparing an indicator substrate in a freshly prepared reaction buffer
2.2. Delivering the desired cofactor to the above substrate solution
2.3. Delivering the indicated kinase to the substrate solution and gently mixing same
2.4. Delivering the compounds in DMSO to the kinase reaction mixture using acoustic technology (Echo550)
2.5. Initiating the reaction (final concentration of ATP: 2 μM, 5 μM and 5 μM respectively) by delivering $^{33}$P-ATP (final specific activity: 0.01 μci/μL) to the reaction mixture
2.6. Incubating the kinase reaction at room temperature for 120 minutes
2.7. Recording the reaction on P81 ion exchange paper (Whatman #3698-915)
2.8. Washing the filter widely with 0.75% phosphoric acid
2.9. Measuring the radioactive phosphorylated substrate remaining on the filter paper.
3. Data analysis: the kinase activity data is expressed as the percentage of the remaining kinase activity in a test sample compared to a reaction with a carrier (dimethyl sulfoxide), and IC$_{50}$ values and curve fitting are obtained using Prism4 software (GraphPad).

4. Experimental conclusion: the results are shown in Table 2.

TABLE 2

Comparison of EGFR, ITK and TEC and BTK kinase inhibitory activities

| Compound No. | EGFR ($IC_{50}$, nM) | ITK ($IC_{50}$, nM) | TEC ($IC_{50}$, nM) | BTK ($IC_{50}$, nM) | The ratio of the activities of EGFR, ITK, TEC and BTK |
|---|---|---|---|---|---|
| 2B | 344 | 8910 | 42 | 5.27 | 65-fold, 1690-fold, 7-fold |
| 4A | 2020 | >10 μM | 169 | 11 | 183-fold, > 909-fold, 15-fold |
| 5B | 829 | 5430 | 74.8 | 2.16 | 383-fold, 2513-fold, 34-fold |
| 6A | 812 | 7320 | 43.2 | 9.58 | 84-fold, 764-fold, 4-fold |
| 7A | 14.5 | 42.2 | 3.39 | 0.73 | 19-fold, 57-fold, 4.6-fold |
| 7B | 33.3 | 1450 | 3.74 | 0.93 | 35-fold, 1559-fold, 4-fold |

Conclusion: the compounds of the present disclosure exhibit a better EGFR, ITK and TEC kinase selectivity.

Experimental Example 3: Pharmacokinetic Study of the Compounds of the Present Disclosure 1. Summary of pharmacokinetic study of the compounds of the present disclosure 1.1 Male CD-1 mice are used as test animals; the LC/MS/MS method is used to determine drug concentrations in plasma of the mice at different time points after intravenous and intragastric administration of test compounds. The pharmacokinetic behaviors of the compounds in mice are studied and the pharmacokinetic characteristics thereof are evaluated.

2. Experiment scheme 2.1 Experimental drugs: test compounds.

2.2 Experimental animals: 4 healthy adult male CD-1 mice, which were divided into 2 groups according to the principle of similar body weight, with 2 mice in each group. The animals were purchased from Shanghai Xipuer-Bikai Experimental Animal Co., Ltd.

2.3 Drug formulation:

An appropriate amount of samples were weighed; a solvent was added, and the mixture was stirred under sonication until a clear state was achieved, and then used for intravenous administration.

An appropriate amount of samples were weighed; a solvent was added; and the mixture was stirred under sonication until an approximately clear solution appeared, and then used for intragastric administration.

2.4 Administration:

4 male CD-1 mice were divided into 2 groups, and fasted overnight. One of the groups was administered intravenously, and the other group was administered intragastrically.

3. Operations

After the test compounds were administered intravenously to male CD-1 mice, 30 μL of blood was collected at 0.0830, 0.25, 0.5, 1, 2, 4, 8 and 24 hours, respectively, and placed in commercial tubes containing $EDTA-K_2$. After the test compounds were administered intragastrically to the other mice, 30 μL of blood was collected at 0.25, 0.5, 1, 2, 4, 6, 8 and 24 hours, respectively, and placed in commercial tubes containing $EDTA-K_2$. The test tubes were centrifuged at 3000 g for 15 minutes to separate the plasma and stored at −60° C. 2 hours after administration, the animals were allowed to eat.

After intravenous and intragastric administration, the content of the compounds to be tested in plasma of the mice was determined by the LC/MS/MS method. The linear range of the method was from 2.00 to 6000 nmol/L; plasma samples were analyzed after treatment of precipitating proteins with acetonitrile.

4. Pharmacokinetic parameter results

TABLE 3

Summary of pharmacokinetic parameter data

| Mode of administration | Dosage | Blood drug concentration Cmax (nM) | Time to peak Tmax (h) | Half-life T1/2 (h) | Apparent volume of distribution Vdss (L/kg) | Clearance rate Cl (mL/min/kg) | Curve area (0-1) AUC0-last (nM · h) | Curve area (0-inf) AUC0-inf (nM · h) | Bioavailability F (%) |
|---|---|---|---|---|---|---|---|---|---|
| 2B intravenous administration | 1 mg/kg | — | — | 1.21 | 0.954 | 13.3 | 2697 | 2720 | — |
| 2B intragastric administration | 2 mg/kg | 400 | 0.25 | 4.88 | — | — | 1259 | 1777 | 23 |
| 5B intravenous administration | 1 mg/kg | — | — | 1.5 | 1.45 | 19.3 | 1821 | 1847 | — |
| 5B intragastric administration | 2 mg/kg | 135 | 0.25 | ND | — | — | 620 | ND | 17 |

Note:
"—": none;
ND: not detected.

Conclusion: the compounds of the present disclosure have a short half-life, wide distribution outside blood plasma and moderate bioavailability.

Experimental Example 4: Study on the Efficacy of the Compounds of the Present Disclosure on Human Lymphoma TMD-8 Cell Subcutaneous Xenograft Models in CB-17 SCID Mice Experimental objective: the anti-tumor effects of the compounds were evaluated in this experiment by using TMD-8 cell subcutaneous xenograft models in CB-17 SCID mice.

Experimental Operations:
(1) Cell Culture:
Human lymphoma TMD-8 cells were cultured in a monolayer configuration in vitro, with culture conditions as follows: RMPJ-1640 medium supplemented with 10% fetal bovine serum, 100 U/mL penicillin and 100 µg/mL streptomycin, and 37° C., 5% $CO_2$ incubator. Conventional digestion treatment with pancreatin-EDTA for passage was carried out twice a week. When the cell saturation was 80% to 90%, and the number reached the requirement, the cells were collected, counted and inoculated.

(2) Tumor Cell Inoculation
0.2 mL ($1 \times 10^7$ cells) of TMD-8 cells (supplemented with matrigel in a volume ratio of 1:1) were subcutaneously inoculated on the right back of each mouse. The grouping and administration were started when the average tumor volume reached about 113 mm$^3$.

(3) Preparation of Test Samples
Compound group to be tested: a quantitative amount of the test compound was weighed in a brown dispensing bottle, and corresponding volume of a solvent was added. Then the mixture was vortexed to obtain a homogeneous suspension or clear solution.

Tumor diameter was measured twice a week with a vernier caliper. The calculation formula of tumor volume was V=0.5a×b$^2$, wherein a and b represent the long and short diameters of the tumor, respectively.

The anti-tumor efficacy of the compound was evaluated by TGI (%) or relative tumor proliferation rate T/C (%). Relative tumor proliferation rate T/C (%)=$T_{RTV}/C_{RTV} \times$ 100% ($T_{RTV}$: RTV of the treatment group; $C_{RTV}$: RTV of the negative control group). The relative tumor volume (RTV) was calculated according to the results of the tumor measurement. The calculation formula was RTV=$V_t/V_0$, wherein $V_0$ was the average tumor volume measured at the beginning of the grouping and administration (i.e., D0), and $V_t$ was the average tumor volume in a certain measurement. $T_{RTV}$ and $C_{RTV}$ were obtained from the data on the same day.

TGI (%) reflected the tumor growth inhibition rate. TGI (%)=[(1−(average tumor volume at the end of administration in a certain treatment group−average tumor volume at the beginning of administration in the treatment group))/(average tumor volume at the end of administration in the solvent control group−average tumor volume at the beginning of administration in the solvent control group)]×100%.

At the end of the experiment, the tumor weight would be detected, and the percentage of T/C$_{weight}$ would be calculated, wherein T$_{weight}$ and C$_{weight}$ represent the tumor weight of the administration group and the solvent control group, respectively.

Statistical Analysis
statistical analysis was performed using SPSS software on the basis of RTV data at the end of the experiment. The comparison between three or more groups was analyzed by one-way ANOVA. If there was homogeneity of variance (F value was not significantly different), the Tukey's test was used for analysis. If there was heterogeneity of variance (F value was significantly different), the Games-Howell test was applied. p<0.05 was considered significantly different.

Experimental conclusion: the results are shown in Table 4.

TABLE 4

Effects of the compounds of the present disclosure on human lymphoma TMD-8 cell subcutaneous xenograft models

| Compound No. | Dosage (mpk) | TGI (%) | T/C | P value |
|---|---|---|---|---|
| 2B | 50, once a day | 102 | 7.7% | ≤0.05 |
| 5B | 50, once a day | 101 | 3.6% | 0.008 |

Conclusion: the compounds of the present disclosure have significant anti-tumor effects compared to the solvent control group.

What is claimed is:
1. A compound of formula (I):

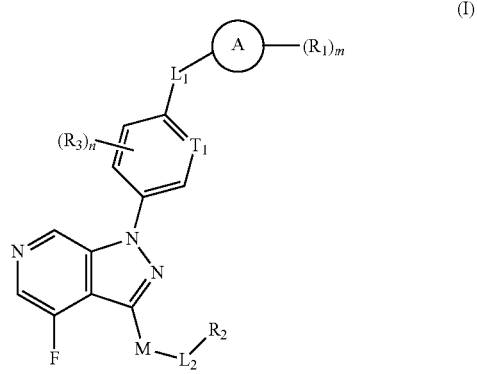

or a pharmaceutically acceptable salt or stereoisomer thereof,
wherein:
$L_1$ is —$CH_2$—, —$CH_2CH_2$—, —C(O)NH—, or —O—;
ring A is phenyl or a 5- or 6-membered heteroaryl, wherein the 5- or 6-membered heteroaryl contains 1, 2, 3, or 4 heteroatoms or heteroatomic groups independently selected from the group consisting of N, NH, O, and S;
each $R_1$ is independently F, Cl, Br, I, CN, $NH_2$, or OH;
m is 0, 1, 2, or 3;
$T_1$ is CH or N;
each $R_3$ is independently F, Cl, Br, I, CN, $NH_2$, or OH;
n is 0, 1, 2, or 3;
M is $C_{3-6}$ cycloalkyl or a 3- to 6-membered heterocycloalkyl, wherein the 3- to 6-membered heterocycloalkyl contains 1, 2, 3, or 4 heteroatoms or heteroatomic groups independently selected from the group consisting of —C(O)—, N, —NH—, —O—, —S—, and —S(O)—, and further wherein the $C_{3-6}$ cycloalkyl or 3- to 6-membered heterocycloalkyl is optionally substituted with 1, 2, or 3 independently selected $R_b$ substituents;
each $R_b$ is independently F, Cl, Br, I, or $CH_3$;
$L_2$ is —$CH_2$—, —$CH_2CH_2$—, —C(O)—, —C(O)NH—, or —O—;

$R_2$ is H, $C_{1-6}$ alkyl, $C_{2-6}$ alkenyl, or $C_{2-6}$ alkynyl, wherein the $C_{1-6}$ alkyl, $C_{2-6}$ alkenyl, or $C_{2-6}$ alkynyl is optionally substituted with 1, 2, or 3 independently selected $R_a$ substituents;

each $R_a$ is independently F, Cl, Br, I, CN, $C_{1-3}$ alkyl, $NH_2$, $NHC_{1-3}$ alkyl, OH, or $OC_{1-3}$ alkyl, wherein each $C_{1-3}$ alkyl, $NHC_{1-3}$ alkyl, or $OC_{1-3}$ alkyl is optionally and independently substituted with 1, 2, or 3 independently selected R substituents; and each R is independently F, Cl, Br, or I;

with the proviso that n and m are not simultaneously 0.

2. The compound according to claim 1, or a pharmaceutically acceptable salt or stereoisomer thereof, wherein $L_1$ is —C(O)NH— or —O—.

3. The compound according to claim 1, or a pharmaceutically acceptable salt or stereoisomer thereof, wherein

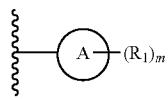

is:

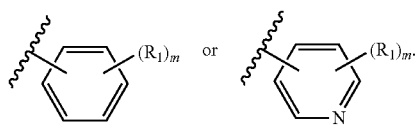

4. The compound according to claim 3, or a pharmaceutically acceptable salt or stereoisomer thereof, wherein

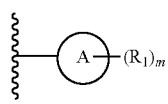

is:

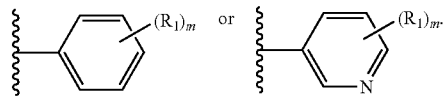

5. The compound according to claim 4, or a pharmaceutically acceptable salt or stereoisomer thereof, wherein

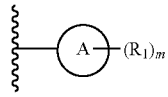

is:

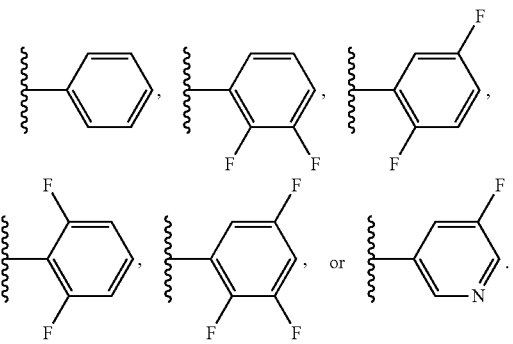

6. The compound according to claim 1, or a pharmaceutically acceptable salt or stereoisomer thereof, wherein M is cyclopropyl, cyclobutyl, cyclopentyl, cyclohexyl, azetidinyl, oxetanyl, piperidinyl, or morpholinyl, wherein the cyclopropyl, cyclobutyl, cyclopentyl, cyclohexyl, azetidinyl, oxetanyl, piperidinyl, or morpholinyl is optionally substituted with 1, 2, or 3 independently selected $R_b$ substituents.

7. The compound according to claim 6, or a pharmaceutically acceptable salt or stereoisomer thereof, wherein M is piperidinyl or morpholinyl.

8. The compound according to claim 1, or a pharmaceutically acceptable salt or stereoisomer thereof, wherein $L_2$ is —C(O)— or —C(O)NH—.

9. The compound according to claim 1, or a pharmaceutically acceptable salt or stereoisomer thereof, wherein $R_2$ is H, $C_{1-3}$ alkyl, $C_{2-4}$ alkenyl, or $C_{2-4}$ alkynyl, wherein the $C_{1-3}$ alkyl, $C_{2-4}$ alkenyl, or $C_{2-4}$ alkynyl is optionally substituted with 1, 2, or 3 independently selected $R_a$ substituents.

10. The compound according to claim 3, or a pharmaceutically acceptable salt or stereoisomer thereof, wherein $R_2$ is H, $CH_3$, $CH=CH_2$, $C\equiv CCH_3$, or $CH_2C\equiv CH$.

11. The compound according to claim 1, or a pharmaceutically acceptable salt or stereoisomer thereof, wherein each $R_a$ is independently F, Cl, Br, I, CN, $CH_3$, $NH_2$, $NHCH_3$, OH, or $OCH_3$.

12. The compound according to claim 1, wherein the compound is of formula (I-1), formula (I-2), or formula (I-3):

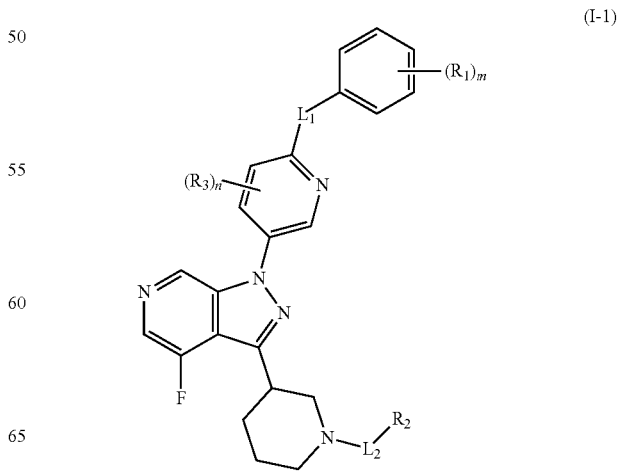

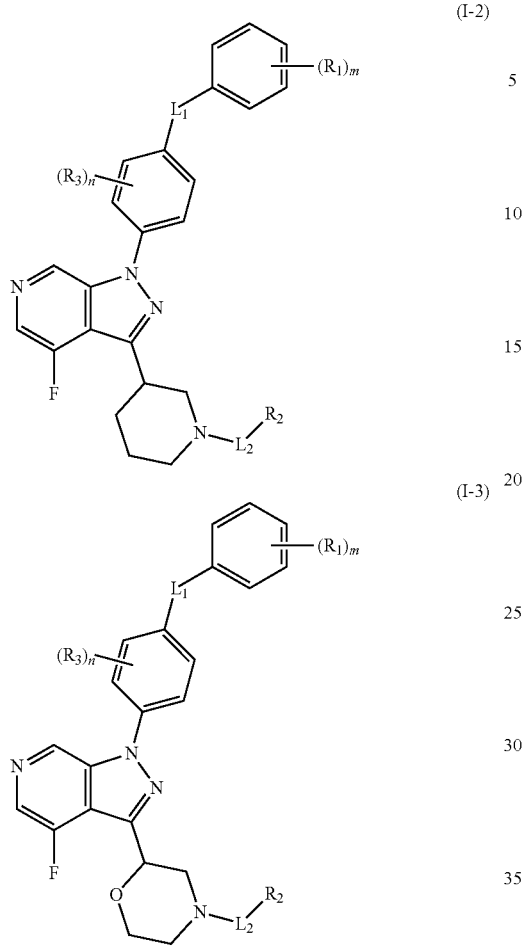
or a pharmaceutically acceptable salt or stereoisomer thereof.
13. The compound according to claim 12, or a stereoisomer thereof, wherein the stereoisomer of the compound is of formula (I-1a), formula (I-1b), formula (I-2a), formula (I-2b), formula (I-3a), or formula (I-3b):
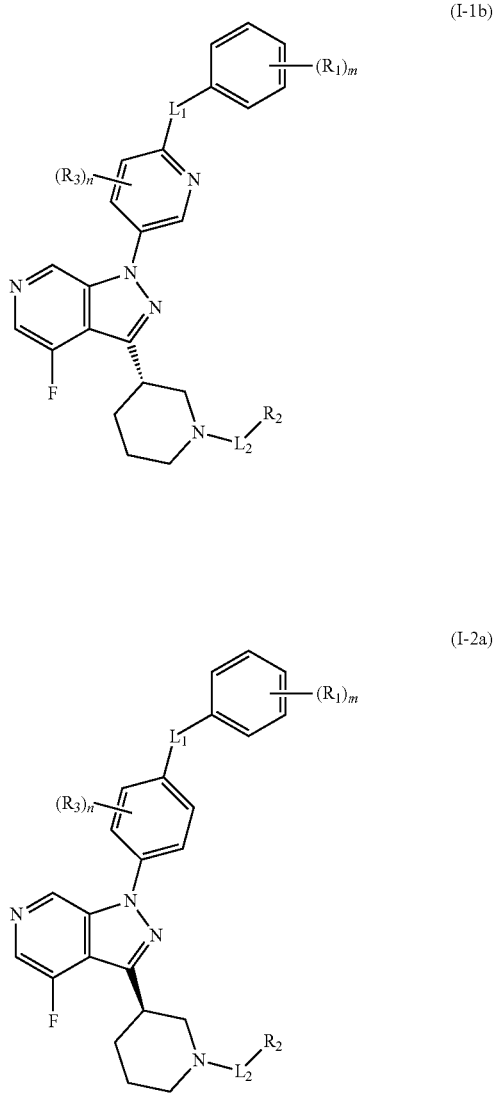
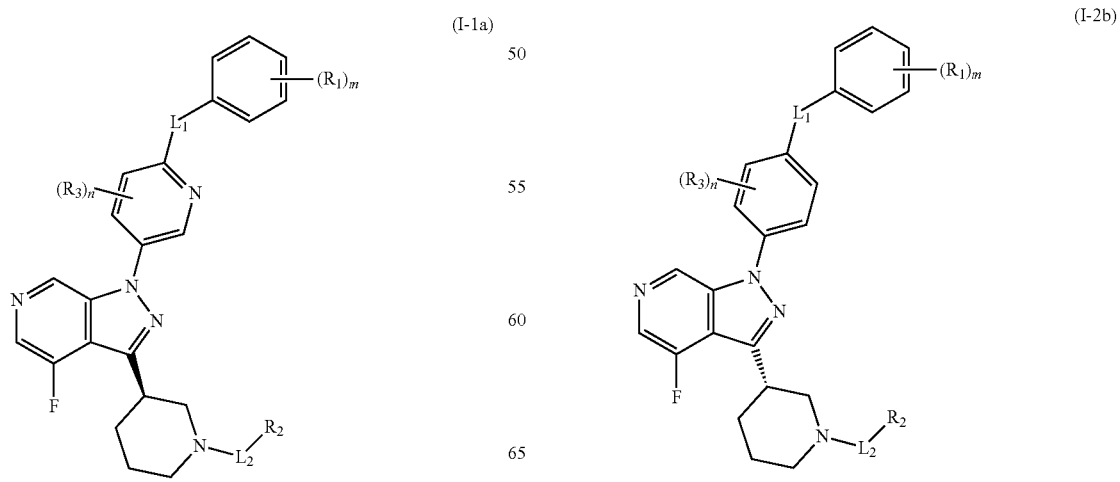

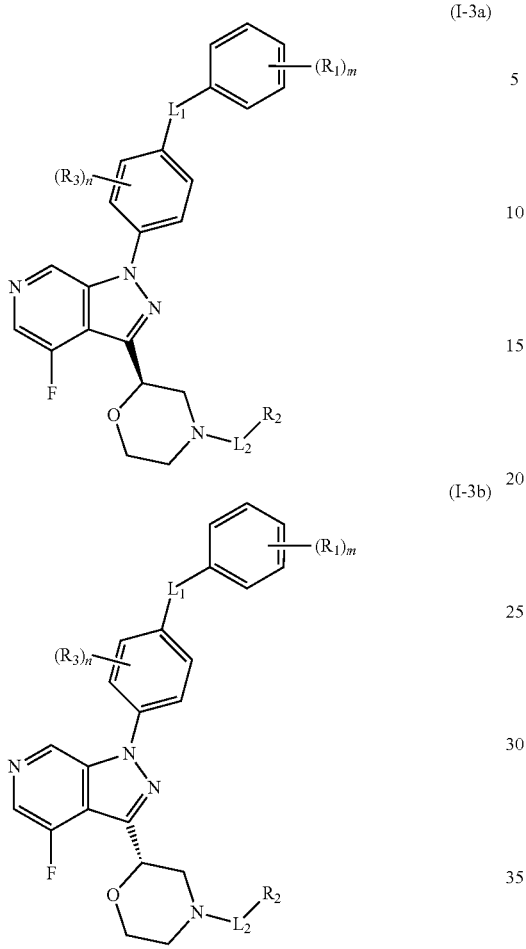
(I-3a)
(I-3b)
or a pharmaceutically acceptable salt thereof.
14. A pharmaceutical composition comprising a pharmaceutically acceptable carrier and a therapeutically effective amount of the compound according to claim 1, or a pharmaceutically acceptable salt or stereoisomer thereof, as an active ingredient.
15. A compound selected from the group consisting of:
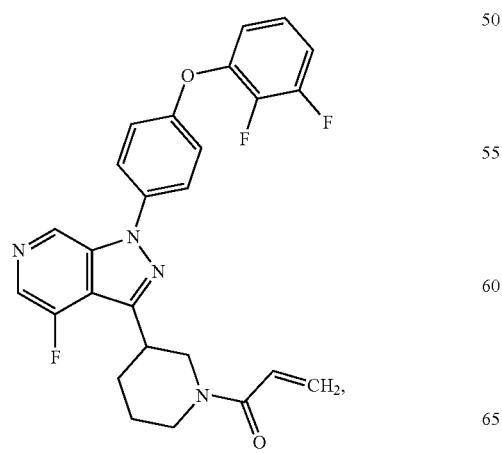
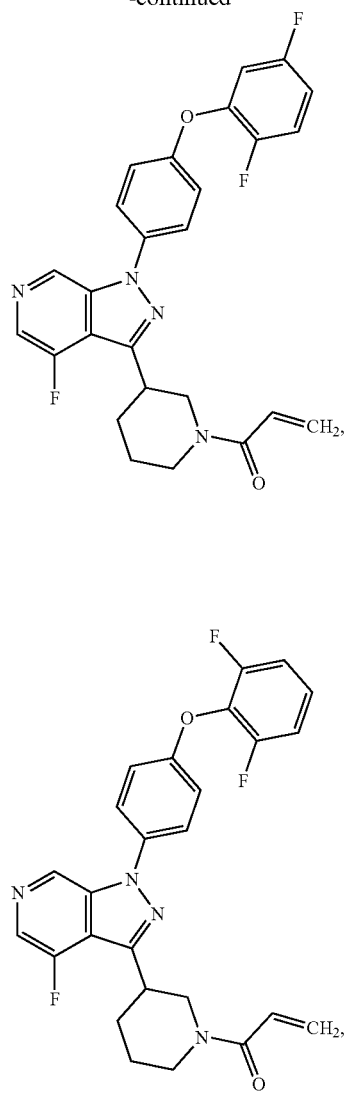

71
-continued
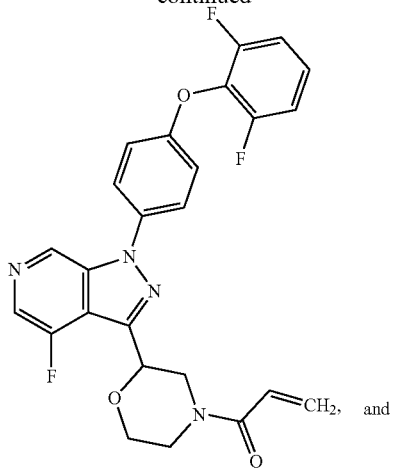
and
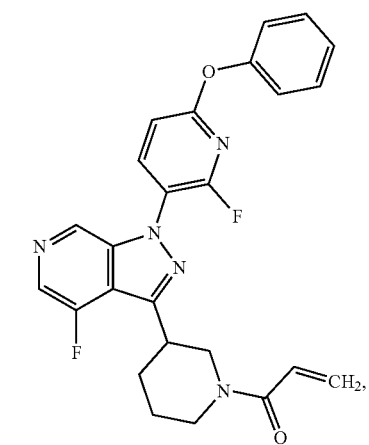
or a pharmaceutically acceptable salt or stereoisomer thereof.
16. The compound according to claim 15, or a stereoisomer thereof, wherein the stereoisomer of the compound is selected from the group consisting of:
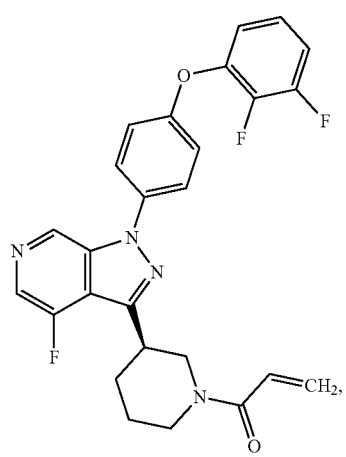
72
-continued
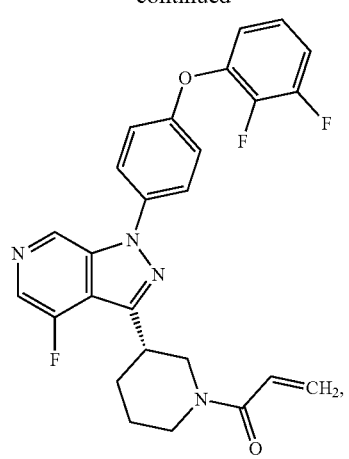
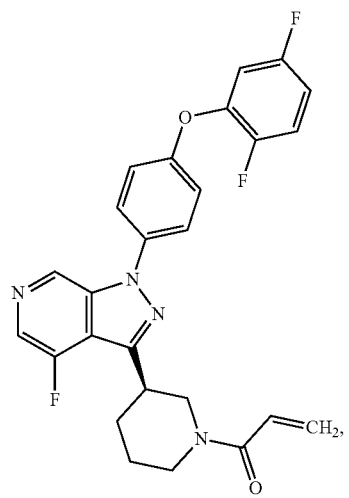

73
-continued
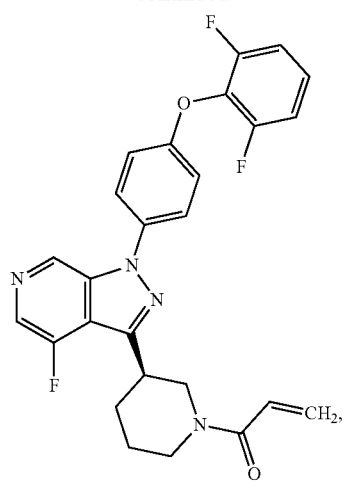
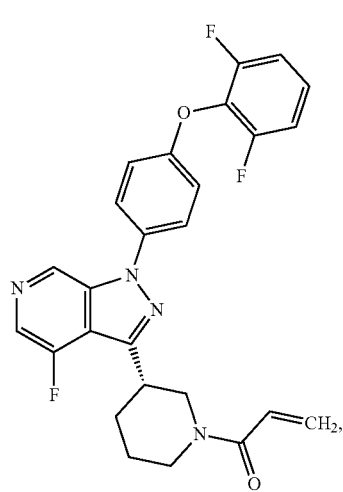
74
-continued
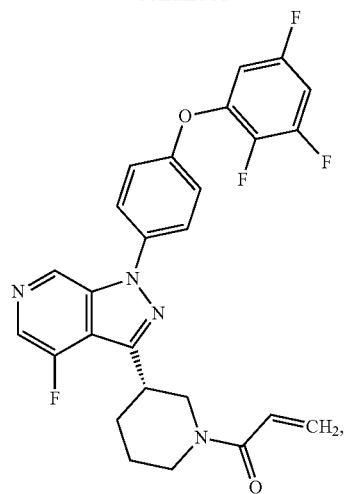
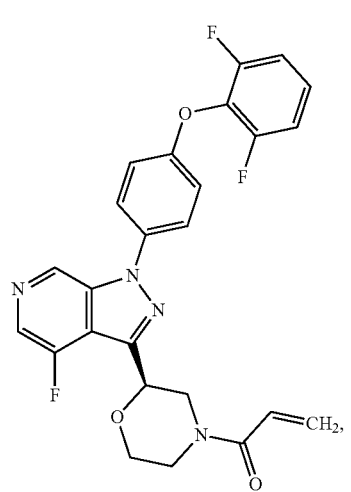

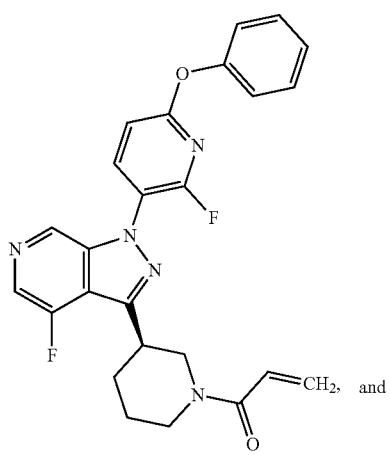
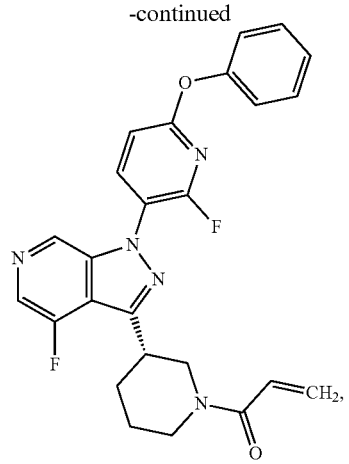
or a pharmaceutically acceptable salt thereof.
* * * * *